(12) United States Patent
Anway et al.

(10) Patent No.: US 9,267,906 B2
(45) Date of Patent: Feb. 23, 2016

(54) BONDLINE EMBEDDED CURRENT SENSOR

(71) Applicant: The Boeing Company, Chicago, IL (US)

(72) Inventors: Carol E. Anway, North Bend, WA (US); Andrew M. Robb, Ravensdale, WA (US); Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 32 days.

(21) Appl. No.: 14/337,095

(22) Filed: Jul. 21, 2014

(65) Prior Publication Data

US 2014/0327433 A1 Nov. 6, 2014

Related U.S. Application Data

(63) Continuation-in-part of application No. 13/085,450, filed on Apr. 12, 2011, now Pat. No. 8,812,251.

(51) Int. Cl.
*G01B 3/00* (2006.01)
*G01N 27/02* (2006.01)
(Continued)

(52) U.S. Cl.
CPC ............ *G01N 27/025* (2013.01); *B29C 65/483* (2013.01); *B29C 65/5021* (2013.01);
(Continued)

(58) Field of Classification Search
CPC .. G01L 3/22; G01N 29/07; G01N 2291/0258; G01N 2291/02818; G01N 29/24; H01F 27/28; H01H 1/0015; G01R 29/00
See application file for complete search history.

(56) References Cited

U.S. PATENT DOCUMENTS 6,384,610 B1 5/2002 Wilson
6,859,757 B2 * 2/2005 Muehl ................... G06Q 10/06
235/375

(Continued)

FOREIGN PATENT DOCUMENTS

EP 0573350 12/1993
EP 0573778 12/1993

(Continued)

OTHER PUBLICATIONS

Jeong-Beom Ihn et al., "Detection and monitoring of hidden fatigue crack growth using a built-in piezoelectric sensor/actuator network: I. Diagnostics", Smart Materials and Structures, Institute of Physics Publishing, 13 (2004) pp. 609-620, Printed in the UK.

(Continued)

*Primary Examiner* — Elias Desta

(57) ABSTRACT

A system for monitoring electrical current passing through a cured bondline may include a current sensor network embedded in an adhesive layer of the cured bondline. The current sensor network may include a plurality of inductive coils and a plurality of current sensor nodes electrically interconnecting the inductive coils to form a plurality of current sensor loops generating induced current in response to a magnetic field associated with an electrical current passing through the adhesive layer. The current sensor nodes may generate current signals representative of the induced current. The current sensor network may include a digital data communications network located external to the cured bondline and receiving the current signals from the current sensor nodes and detecting and monitoring electrical current passing through the cured bondline based on the current signals.

20 Claims, 15 Drawing Sheets

(51) Int. Cl.
- *B29C 65/48* (2006.01)
- *B29C 65/50* (2006.01)
- *B29C 65/82* (2006.01)
- *B29C 65/00* (2006.01)
- *G01N 27/20* (2006.01)
- *B64C 3/20* (2006.01)
- *B64D 45/00* (2006.01)
- *G01M 5/00* (2006.01)
- *B29L 31/30* (2006.01)
- *B29K 105/20* (2006.01)
- *F16B 11/00* (2006.01)
- *B64C 1/00* (2006.01)

(52) U.S. Cl.
CPC ......... *B29C65/5028* (2013.01); *B29C 65/5057* (2013.01); *B29C 65/8276* (2013.01); *B29C 65/8284* (2013.01); *B29C 66/1122* (2013.01); *B29C 66/45* (2013.01); *B29C 66/721* (2013.01); *B64C 3/20* (2013.01); *B64D 45/00* (2013.01); *G01M 5/0033* (2013.01); *G01M 5/0083* (2013.01); *G01M 5/0091* (2013.01); *G01N 27/026* (2013.01); *G01N 27/20* (2013.01); *B29C 65/4835* (2013.01); *B29C 65/8292* (2013.01); *B29C 66/71* (2013.01); *B29C 66/7212* (2013.01); *B29C 66/72141* (2013.01); *B29C 66/72143* (2013.01); *B29C 66/7392* (2013.01); *B29C 66/7394* (2013.01); *B29C 66/73921* (2013.01); *B29C 66/73941* (2013.01); *B29K 2105/206* (2013.01); *B29L 2031/3076* (2013.01); *B29L 2031/3079* (2013.01); *B29L 2031/3082* (2013.01); *B29L 2031/3085* (2013.01); *B64C 2001/0072* (2013.01); *B64D 2045/0085* (2013.01); *F16B 11/006* (2013.01)

(56) References Cited

U.S. PATENT DOCUMENTS

| | | | |
|---|---|---|---|
| 7,367,236 | B2 | 5/2008 | Georgeson et al. |
| 7,414,416 | B2 | 8/2008 | Watkins, Jr. et al. |
| 8,264,215 | B1 | 9/2012 | Kovach et al. |
| 2007/0166831 | A1 | 7/2007 | Watkins, Jr. et al. |
| 2009/0294022 | A1 | 12/2009 | Hayes et al. |
| 2010/0005896 | A1 | 1/2010 | Miller et al. |

FOREIGN PATENT DOCUMENTS

| | | |
|---|---|---|
| EP | 2070688 | 6/2009 |
| WO | WO0046593 | 8/2000 |
| WO | WO03076953 | 9/2003 |

OTHER PUBLICATIONS

Jeong-Beom Ihn et al., "Detection and monitoring of hidden fatigue crack growth using a built-in piezoelectric sensor/actuator network: II. Validation using riveted joints and repair patches", Smart Materials and Structures, Institute of Physics Publishing, 13 (2004) pp. 621-630, Printed in the UK.

Jeong-Beom Ihn et al., "Pitch-catch Active Sensing Methods in Structural Health Monitoring for Aircraft Structures", Structural Health Monitoring, Sage Publications, 2008, vol. 7(1), pp. 5-19.

Tom Zhuang, "Design of Smart Adhesive Films for Bondline Integrity Monitoring", Feb. 8, 2012, Structures and Composites Laboratory (SACL) at Stanford University, Palo Alto, California, XP55025731, Retrieved from internet at URL: structure.stanford.edu/documents%5Cprojects%5Czhuang.pdf (retrieved on Jun. 1, 2012), 8 pages.

Alan Wilson et al., "MEMS Adhesive Bond Degradation Sensor", Analatom Inc., Sunnyvale, CA, Aeronautical and Maritime Research Lab, Melbourne, Australia, Dec. 15, 2000, 8 pages.

PCT International Search Report and Written Opinion for counterpart International Application PCT/US2012/024425, Mailed May 10, 2012, 13 pages.

Daniel J. Kovach et al., "A Novel Method for Direct Measurement of Current Flows in Fastener Arrays", International Conference on Lightning and Static Electricity, Oxford, England 2011.

\* cited by examiner

BONDLINE EMBEDDED CURRENT SENSOR

CROSS-REFERENCE TO RELATED APPLICATIONS

The present application is a continuation-in-part of and claims priority to U.S. patent application Ser. No. 13/085,450, now U.S. Pat. No. 8,812,251, entitled SYSTEM AND METHOD FOR MONITORING BONDING INTEGRITY filed on Apr. 12, 2011, the entire contents of which is incorporated by reference herein.

FIELD

The disclosure relates generally to systems and methods for monitoring bonding integrity, and more particularly, to systems and methods for monitoring adhesive bonding integrity of bonded structural assemblies, such as composite structural assemblies. In addition, the disclosure relates generally to systems and methods for monitoring electrical current flow, and more particularly, to systems and methods for monitoring electrical current flow through an adhesively bonded joint.

BACKGROUND

The manufacture and assembly of structures and structural components has increasingly involved the use of bonded joints or bondlines, such as adhesive bonded joints or bondlines, instead of fastener devices, to bond or join the structural components together. Adhesive bonded joints may be used in bonding of composite structural components in combination with other composites or other materials such as metal. In this regard, adhesive bonded composite structures and structural components may typically be used in the manufacture and assembly of aircraft, spacecraft, rotorcraft, watercraft, automobiles, trucks, buses, and other vehicles and structures due to the design flexibility and low weight of such composite structures and structural components.

Known inspection methods and devices exist for assessing the integrity of adhesive bonded joints or bondlines in order to measure the quality, soundness, effectiveness, performance, strength, or other characteristics of the adhesive bond, as well as to assess the ability of the adhesive bond to function reliably as required throughout the predicted lifetime of the bonded structure or structural components. Such known inspection methods and devices may include a variety of time-consuming techniques such as visual inspection, localized non-destructive inspection methods, laser bond and ultrasonic inspection devices, or other known methods and devices. These known inspection methods and devices may require that the hardware be pulled out of service for the inspection and may not have the ability to interrogate the bondline while the component part is in-service. In addition, such inspection methods and devices may increase costs and flow time to the process of assuring bondline integrity. Moreover, such known inspection methods and devices may only be carried out at certain times or on a periodic basis, rather than having the information about the bondline integrity available at all times on demand and available on a continuous, real time basis.

In particular, known visual inspection and localized non-destructive inspection methods and devices may not be effective where visual access to the adhesive bonded joints or bondlines is limited or not possible, for example, if such adhesive bonded joints or bondlines are located in a remote or interior location or beneath the surface. Access to interior bonded joints and bondlines may be difficult or not possible without disassembly or damage to the structures or structural components, such as removing a part or drilling a hole into a structure for insertion of a measurement tool. In addition, ultrasonic inspections may require specialized equipment, substantial operator training, and effective access to the structural component.

In addition, known methods and devices exist for monitoring the health of a composite structure with the use of external sensors. For example, U.S. Patent Publication Number 2007/0166831 A1 to Watkins, Jr. et al., discloses a method for monitoring the health of a composite structure by disposing a condition sensor on the surface of the composite structure. However, positioning sensors on the external surface of the structure may provide measurements of the whole structure including measurements through the structural components and the bondline. Such known methods and devices may provide only indirect and less accurate measurements of bondline characteristics and not direct and more accurate measurements of bondline characteristics at or within the bondline. In addition, alignment and positioning of external sensors may be complicated by accessibility to the structure or structural component, for example, inaccessibility to one side of a composite sandwich structure.

Accordingly, there is a need in the art for an improved system and method for monitoring bonding integrity directly at or within adhesive bonded joints or bondlines of structures or structural assemblies where such improved system and method provide advantages over known systems and methods.

A related aspect of monitoring the integrity of adhesively-bonded joints is with regard to detecting and monitoring high-intensity transient electrical currents that may pass through bonded joints. For example, aircraft must be capable of withstanding high-intensity current due to lightning strikes. In view of the undesirable effects of high-intensity electrical current on adhesive, and considering the increasing use of adhesively-bonded joints in the primary structure of an aircraft, it is becoming necessary to detect and monitor electrical current flow through bonded joints as may occur in the event of a lightning strike. In this regard, it is necessary to understand the distribution of current flow from a lightning strike toward and through bonded joints to facilitate the testing, design, and development of aircraft structures capable of withstanding or avoiding excessively-high current flow through bonded joints. As indicated above, known methods for assessing the integrity of adhesively-bonded joints are limited to time-consuming techniques such as visual inspection, localized non-destructive inspection methods, the use of laser bond and ultrasonic inspection devices, or other known methods and devices.

Accordingly, there exists a need in the art for a system and method for detecting and monitoring electrical current flow through bonded joints so that appropriate lighting protection may be provided to such bonded joints.

SUMMARY

This need for a system and method for monitoring bonding integrity directly at or within adhesive bonded joints or bondlines of structures or structural assemblies is satisfied. As discussed in the below detailed description, embodiments of the system and method may provide significant advantages over existing systems and methods.

In an embodiment of the disclosure, there is provided a system for monitoring adhesive integrity within a cured bondline of a bonded structural assembly. The system comprises a bonded structural assembly having a cured bondline. The cured bondline comprises an adhesive layer, a scrim ply layer integrated with the adhesive layer, and an electrical sensor network integrated with the scrim ply layer. The system further comprises an electrical power source for providing electrical power to the electrical sensor network. The system further comprises a digital data communications network for retrieving and processing data from the electrical sensor network. The electrical sensor network monitors adhesive integrity within the cured bondline on demand by interpreting changes in local dynamic responses and electromechanical properties directly measured within the cured bondline.

In another embodiment of the disclosure, there is provided a system for monitoring adhesive integrity within a cured bondline of a bonded composite lamina assembly. The system comprises a bonded composite lamina assembly having a cured bondline. The cured bondline comprises an adhesive layer, a scrim ply layer integrated with the adhesive layer, and an electrical sensor network integrated with the scrim ply layer. The system further comprises a wireless electrical power source for providing electrical power to the electrical sensor network. The system further comprises a wireless digital data communications network for retrieving and processing data from the electrical sensor network. The electrical sensor network monitors adhesive integrity within the cured bondline on demand by interpreting changes in local dynamic responses and electromechanical properties directly measured within the cured bondline.

In another embodiment of the disclosure, there is provided a method for monitoring adhesive integrity within a cured bondline of a bonded structural assembly. The method comprises providing a bonded structural assembly having a cured bondline. The cured bondline comprises an adhesive layer, a scrim ply layer integrated with the adhesive layer, and an electrical sensor network integrated with the scrim ply layer. The method further comprises activating the electrical sensor network to monitor adhesive integrity of the cured bondline on demand by interpreting changes in local dynamic responses and electromechanical properties directly measured within the cured bondline. The method further comprises retrieving and processing adhesive integrity data of the cured bondline from the electrical sensor network via a digital data communications network.

Also disclosed is a current detection system for monitoring electrical current passing through a cured bondline bonding a first structure to a second structure of a structural assembly. The structural assembly may be included in an aircraft or in any vehicular or non-vehicular structure. The current detection system may include a current sensor network embedded in an adhesive layer of the cured bondline. The current sensor network may include a plurality of inductive coils and a plurality of current sensor nodes electrically interconnecting the inductive coils to form a plurality of current sensor loops generating induced current in response to a magnetic field associated with an electrical current passing through the adhesive layer. The current sensor nodes may generate current signals representative of the induced current. The current sensor network may include a digital data communications network located external to the cured bondline and receiving the current signals from the current sensor nodes and detecting and monitoring electrical current passing through the cured bondline based on the current signals.

In a further embodiment, disclosed is a method for monitoring electrical current passing through a cured bondline. The method may include passing an electrical current through an adhesive layer of a cured bondline of a structural assembly. The electrical current may have a magnetic field associated therewith. The adhesive layer may contain a current sensor network including a plurality of inductive coils electrically interconnected at a plurality of current sensor nodes and forming a plurality of current sensor loops. The method may include inducing an induced current in the current sensor loops in response to the magnetic field, and generating, at the current sensor nodes, current signals representative of the induced current. The method may additionally include transmitting the current signals to a digital data communications network located external to the cured bondline, and detecting and monitoring the electrical current using the digital data communications network based on the current signals.

The features, functions, and advantages that have been discussed can be achieved independently in various embodiments of the disclosure or may be combined in yet other embodiments further details of which can be seen with reference to the following description and drawings.

BRIEF DESCRIPTION OF THE DRAWINGS

The disclosure can be better understood with reference to the following detailed description taken in conjunction with the accompanying drawings which illustrate preferred and exemplary embodiments, but which are not necessarily drawn to scale, wherein.

DETAILED DESCRIPTION

Disclosed embodiments will now be described more fully hereinafter with reference to the accompanying drawings, in which some, but not all of the disclosed embodiments are shown. Indeed, several different embodiments may be provided and should not be construed as limited to the embodiments set forth herein. Rather, these embodiments are provided so that this disclosure will be thorough and complete and will fully convey the scope of the disclosure to those skilled in the art. The following detailed description is of the best currently contemplated modes of carrying out the disclosure. The description is not to be taken in a limiting sense, but is made merely for the purpose of illustrating the general principles of the disclosure, since the scope of the disclosure is best defined by the appended claims.

Figure 1:
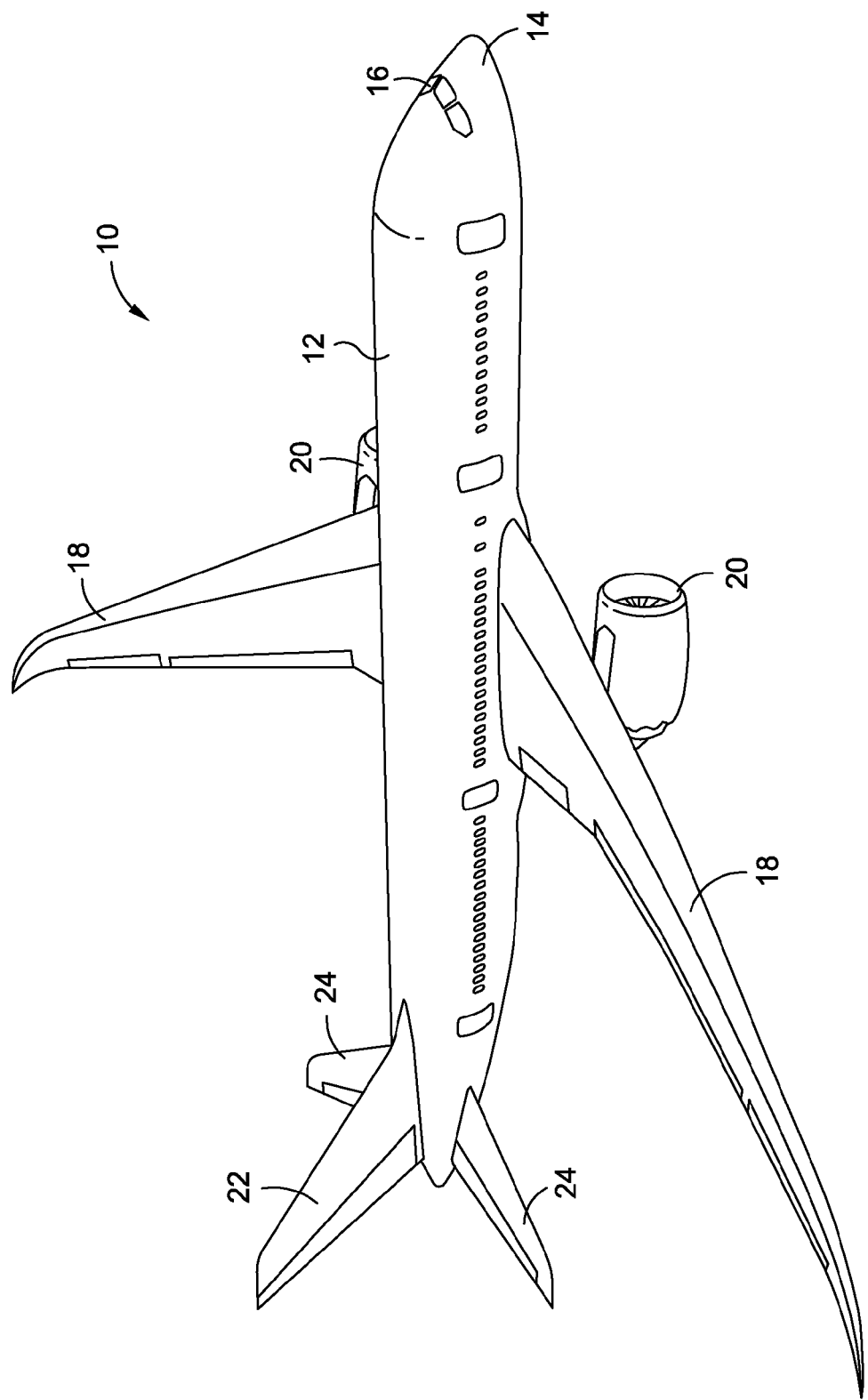
FIG. 1 is an illustration of a perspective view of an exemplary aircraft for which one of the embodiments of the system and method of the disclosure may be used.

Now referring to the Figures, FIG. 1 is an illustration of a perspective view of an exemplary prior art aircraft 10 for which one of the embodiments of a system 30 (see FIG. 2) or a system 100 (see FIG. 3), or a method 200 (see FIG. 9) for monitoring adhesive integrity may be used. The aircraft 10 comprises a fuselage 12, a nose 14, a cockpit 16, wings 18 operatively coupled to the fuselage 12, one or more propulsion units 20, a tail vertical stabilizer 22, and one or more tail horizontal stabilizers 24. Although the aircraft 10 shown in FIG. 1 is generally representative of a commercial passenger aircraft, the systems 30, 100 and method 200 disclosed herein may also be employed in other types of aircraft. More specifically, the teachings of the disclosed embodiments may be applied to other passenger aircraft, cargo aircraft, military aircraft, rotorcraft, and other types of aircraft or aerial vehicles, as well as aerospace vehicles such as satellites, space launch vehicles, rockets, and other types of aerospace vehicles. It may also be appreciated that embodiments of systems, methods and apparatuses in accordance with the disclosure may be utilized in other vehicles, such as boats and other watercraft, trains, automobiles, trucks, buses, and other types of vehicles.

Figure 2:
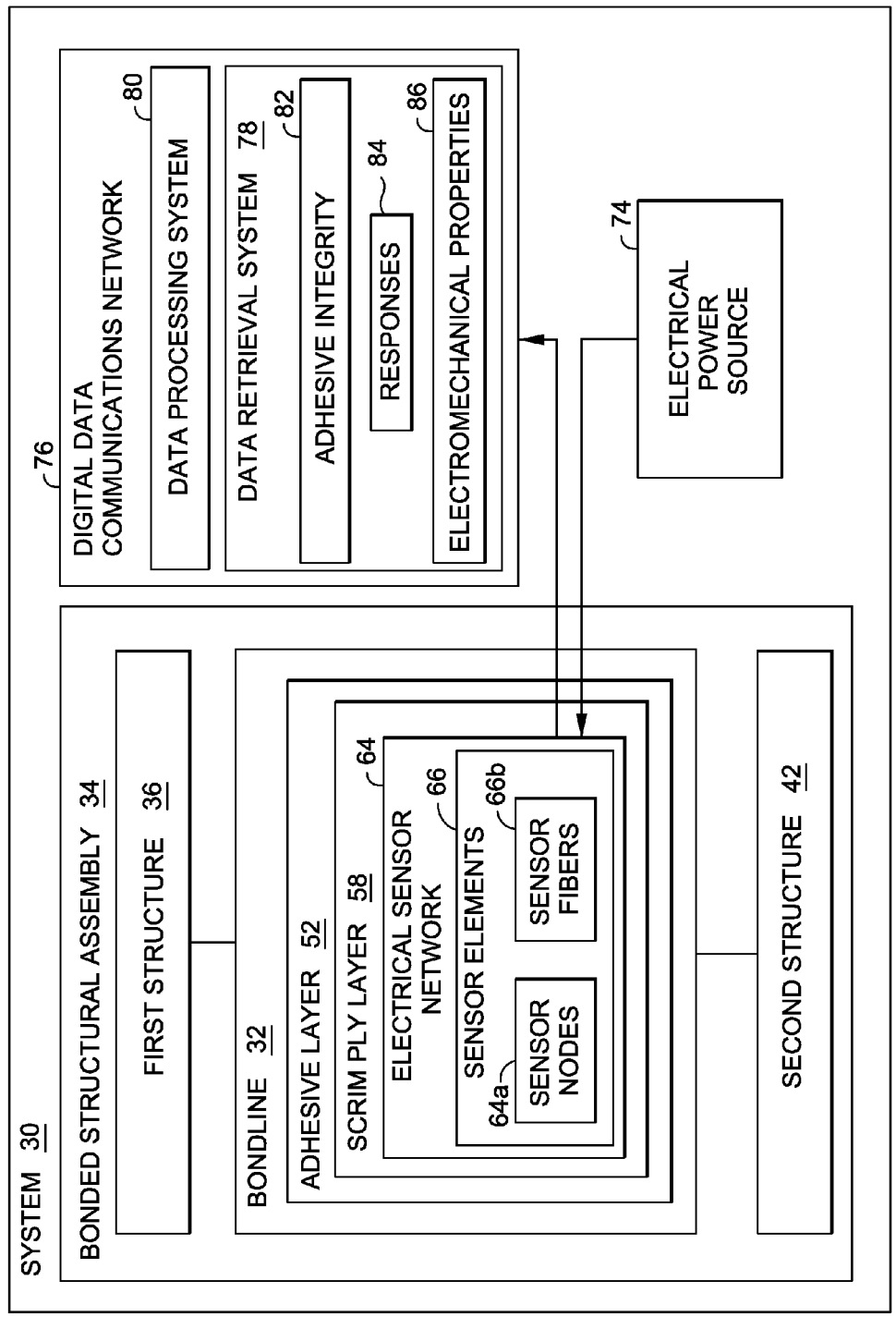
FIG. 2 is an illustration of a block diagram of one of the embodiments of a system for monitoring adhesive integrity of the disclosure.

FIG. 2 is an illustration of a block diagram of one of the embodiments of the system 30 for monitoring adhesive integrity. In one embodiment of the disclosure, there is provided the system 30 for monitoring adhesive integrity within a cured bondline 32 or joint of a bonded structural assembly 34. As used herein, the term "adhesive integrity" means a measure of the quality, soundness, effectiveness, performance, and strength of an adhesive bond and the ability of the adhesive bond to function reliably as required throughout the predicted lifetime of a bonded structural assembly or structure.

Figure 4A:
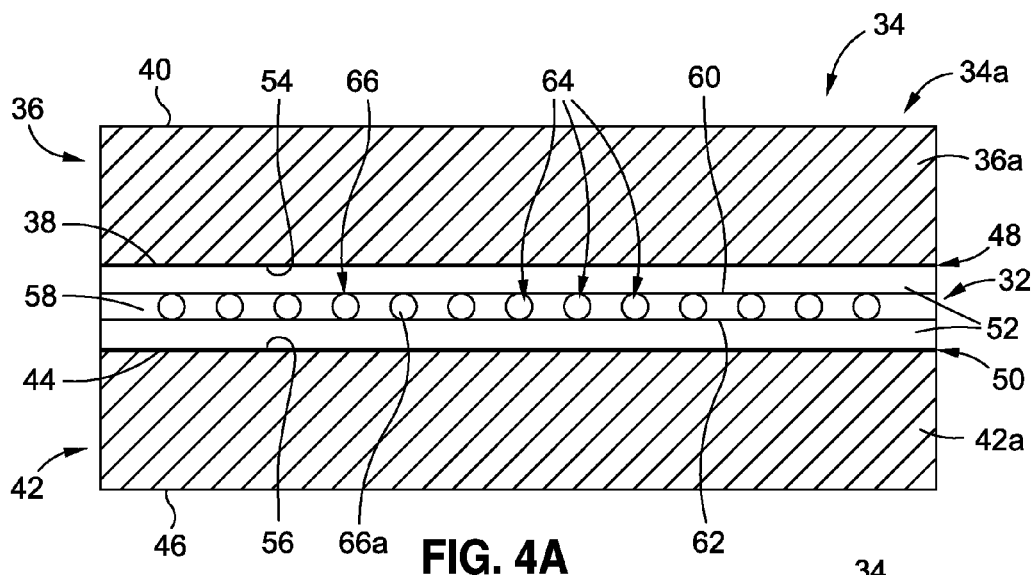
FIG. 4A is an illustration of a partial cross-sectional view of an embodiment of a bonded structure having one of the embodiments of the system of the disclosure.
Figure 4B:
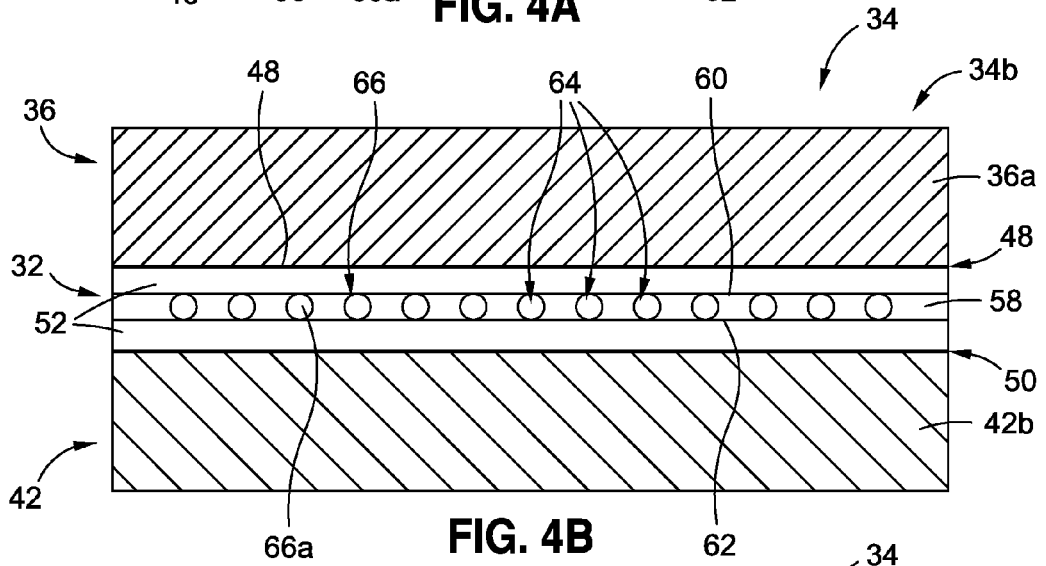
FIG. 4B is an illustration of a partial cross-sectional view of another embodiment of a bonded structure having one of the embodiments of the system of the disclosure.
Figure 4C:
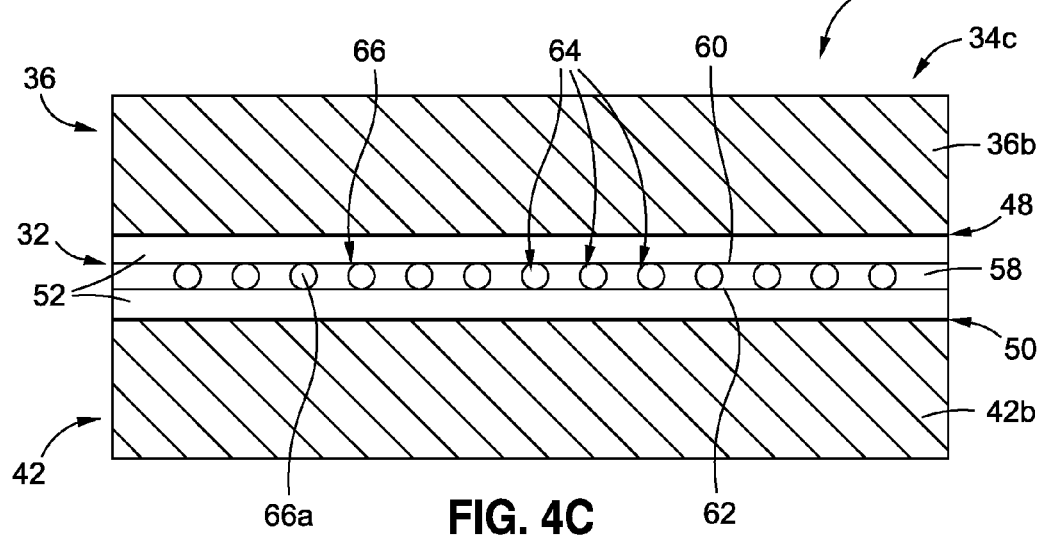
FIG. 4C is an illustration of a partial cross-sectional view of another embodiment of a bonded structure having one of the embodiments of the system of the disclosure.

The system 30 comprises the bonded structural assembly 34 having the cured bondline 32 or joint. As shown in FIGS. 4A-4C, the bonded structural assembly 34 may comprise a first structure 36 and a second structure 42. The first structure 36 has a first side 38 and a second side 40. The second structure 42 has a first side 44 and a second side 46. The first structure 36 may be made of a composite material, a metal material, a combination of a composite material and a metal material, or another suitable material. The second structure 36 may be made of a composite material, a metal material, a combination of a composite material and a metal material, or another suitable material. Preferably, the composite material for the first structure 36 and/or the second structure 42 comprises polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. Exemplary composite material may typically comprise a reinforcement fiber, such as reinforcement fabric, dispersed in a thermoplastic or thermoset polymer matrix. Reinforcement fabrics may comprise fibers made of metallic, carbon, glass, boron, ceramic, and polymeric fibers. The reinforcement fibers may be in woven or non-woven mats, or they may be dispersed in the matrix. Matrix material may comprise thermoplastic materials such as polyamides, polyolefins and fluoropolymers, and thermosets such as epoxies and polyesters. Preferably, the metal material for the first structure 36 and/or the second structure 42 comprises aluminum, stainless steel, titanium, alloys thereof, or another suitable metal or metal alloy.

FIG. 4A is an illustration of a partial cross-sectional view of an embodiment of a bonded structure 34a having a first structure 36a made of one material, such as a metal, and having a second structure 42a made of the same material, such as a metal, as the material of the first structure 36a. FIG. 4B is an illustration of a partial cross-sectional view of another embodiment of a bonded structure 34b having the first structure 36a made of one material, such as a metal, and having a second structure 42b made of a different material, such as a composite, than the material of the first structure 36a. FIG. 4C is an illustration of a partial cross-sectional view of another embodiment of a bonded structure 34c having a first structure 36b made of one material, such as a composite, and having the second structure 42b made of the same material, such as a composite, as the material of the first structure 36b.

As shown in FIGS. 4A-4C, the cured bondline 32 or joint of the bonded structural assembly 34 comprises an adhesive layer or layers 52. As shown in FIG. 4A, the adhesive layer 52 has a first side 54 and a second side 56. The adhesive layer or layers 52 may comprise an adhesive material such as an epoxy adhesive, a polyurethane adhesive, a toughened acrylic adhesive, or another suitable adhesive. Epoxy adhesives generally have good strength, low shrinkage, and produce strong durable bonds with most materials. Polyurethane adhesives generally are fast curing, provide strong resilient joints which are impact resistant, and have good low temperature strength. Toughened acrylic adhesives generally are fast curing, have high strength and toughness, and bond well to a variety of materials.

As shown in FIG. 2, the cured bondline 32 further comprises a scrim ply layer 58 integrated with the adhesive layer or layers 52 (see also FIGS. 4A-4C and 5A-5B). As shown in FIG. 4A, the scrim ply layer 58 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 is preferably multifunctional and acts as an adhesive layer by being integrated in the adhesive layers 52 and also acts as a bondline monitoring system.

As shown in FIGS. 4A-4C, the cured bondline 32 further comprises an electrical sensor network 64 integrated with the scrim ply layer 58. The electrical sensor network 64 preferably comprises a plurality of spaced sensor elements 66. The sensor elements 66 may comprise active sensor nodes 66a (see FIG. 6), active sensor fibers 66b (see FIG. 7), active sensor wires (not shown), sensor fiber optic wires (not shown), sensor coatings on fibers (not shown), carbon nanotubes (not shown), passive sensors, or another suitable sensor element. The sensor elements 66 may be comprised of a matrix of high-resistivity, insulative thermoplastic or thermoset polymer and conductive fillers, such as carbon black, carbon nanotubes, and metallic particles, such as silver, nickel and aluminum, although other conductive and semi-conductive particles such as metallic oxides may be used. The sensor elements 66 may also comprise electrode sensors, piezoelectric sensors, pulse-echo (PE) sensors, pitch-catch active sensors, through transmission (TT) sensors, shear wave sensors, resonance sensors, mechanical impedance sensors, lamb wave sensors, rayleigh wave sensors, stoneley wave sensors, or other suitable sensors. Preferably, the sensor elements 66 are active sensors. However, passive sensors may also be used. Active sensors may generate electric current or voltage directly in response to environmental stimulation. Passive sensors may produce a change in some passive electrical quantity, such as capacitance, resistance, or inductance, as a result of stimulation and typically may require additional electrical energy for excitation. Some RFID devices may be active and some RFID devices may be passive.

The sensor elements 66 may be removable and placed manually on the scrim ply layer 58 integrated with the adhesive layer 52 and later removed. Alternatively, the sensor elements 66 may be bonded or otherwise attached to or within the scrim ply layer 58 by an adhesive or one or more mechanical fasteners (not shown). The sensor elements 66 may be small discrete sensors in the form of strips or electrodes covering some or substantially all of the surface portions of the scrim ply layer 58 or in the form of mats, fibers or woven sheets attached to or on the scrim ply layer 58.

The system 30 integrates the sensing of the cured bondline 32 into the bonded structural assembly 34 and provides a method to interrogate the characteristics and integrity of the cured bondline 32 on demand or continuously. The smart adhesive layer 52 and the scrim ply layer 58 may be a permanent part of the bonded structural assembly 34. The monitoring system 30 provides for an internal electrical sensor network 64 and internal sensor elements 66 at or within the cured bondline 32 to provide for direct measurement and assessment of the bondline characteristics and bondline integrity directly at or within the cured bondline 32 itself.

Figure 6:
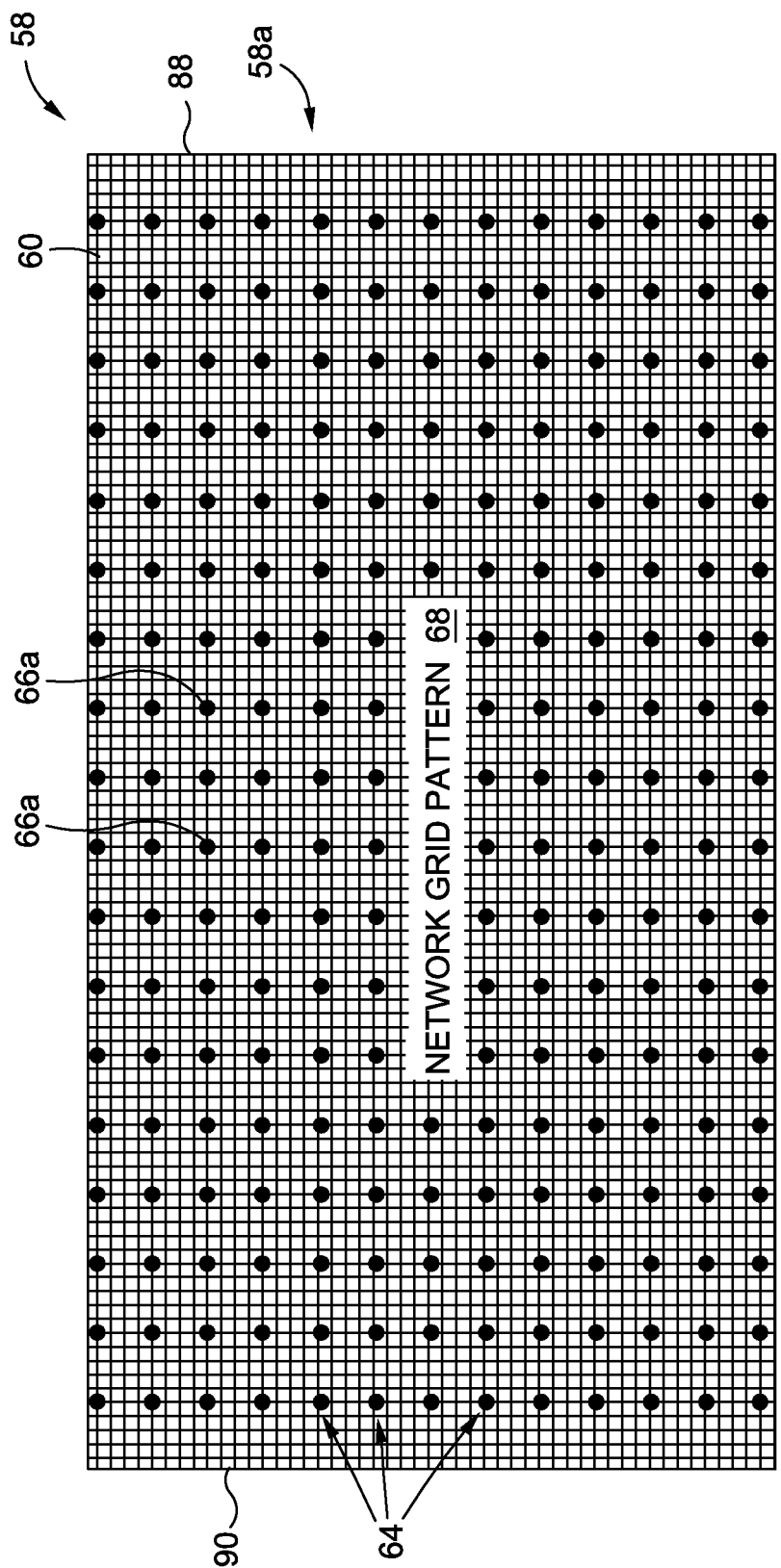
FIG. 6 is an illustration of a top view of one of the embodiments of a scrim ply layer with active sensor nodes.

The sensor elements 66 preferably have modalities based on ultrasonic wave propagation and electromechanical impedance sensing. In order to enable the smart scrim ply layer 58, the sensor elements 66 may be integrated into the woven or random mat fiber layer of the scrim material. In one embodiment, scrim material with the sensor elements 66 may be laminated into the adhesive layer 52 to provide an integrated film adhesive scrim ply layer 58 (see FIG. 6) with sensing capabilities. FIG. 6 is an illustration of a top view of one of the embodiments of the scrim ply layer 58 in the form of a scrim ply layer 58a with an electrical sensor network 64 having sensor elements 66 in the form of active sensor nodes 66a integrated into or attached onto the scrim ply layer 58. As shown in FIG. 6, the sensor nodes 66a form a network grid pattern 68. As shown in FIGS. 4A and 6, the scrim ply layer 58 has a first side 60 (see FIGS. 4A and 6), a second side 62 (see FIG. 4A), a first end 88 (see FIG. 6) and a second end 90 (see FIG. 6).

Figure 5A:
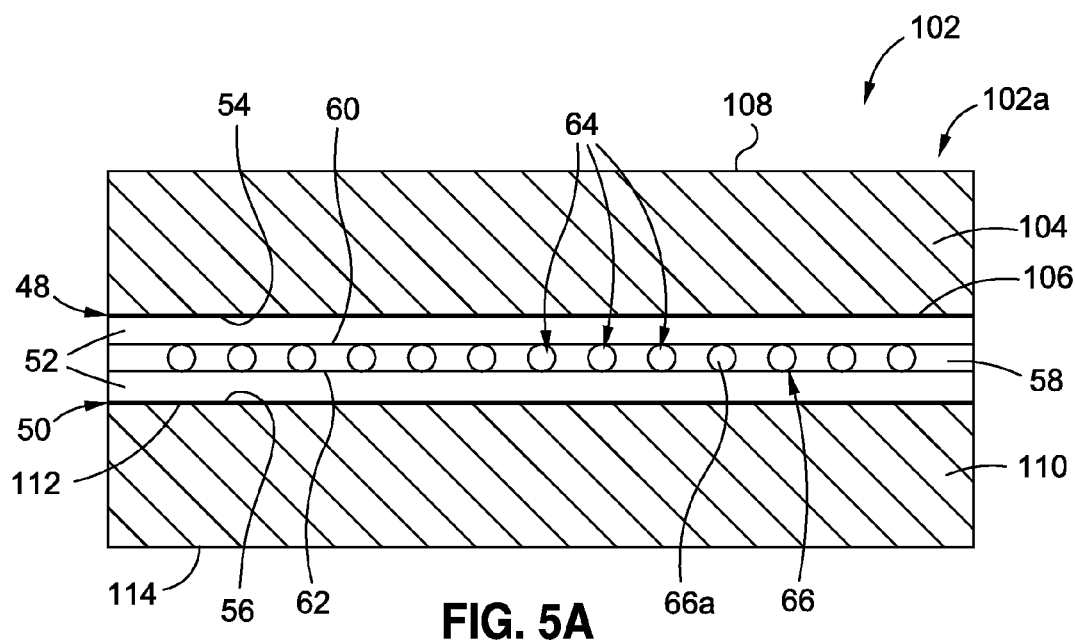
FIG. 5A is an illustration of a partial cross-sectional view of an embodiment of a bonded structure having one of the embodiments of the electrical sensor network of the disclosure.
Figure 5B:
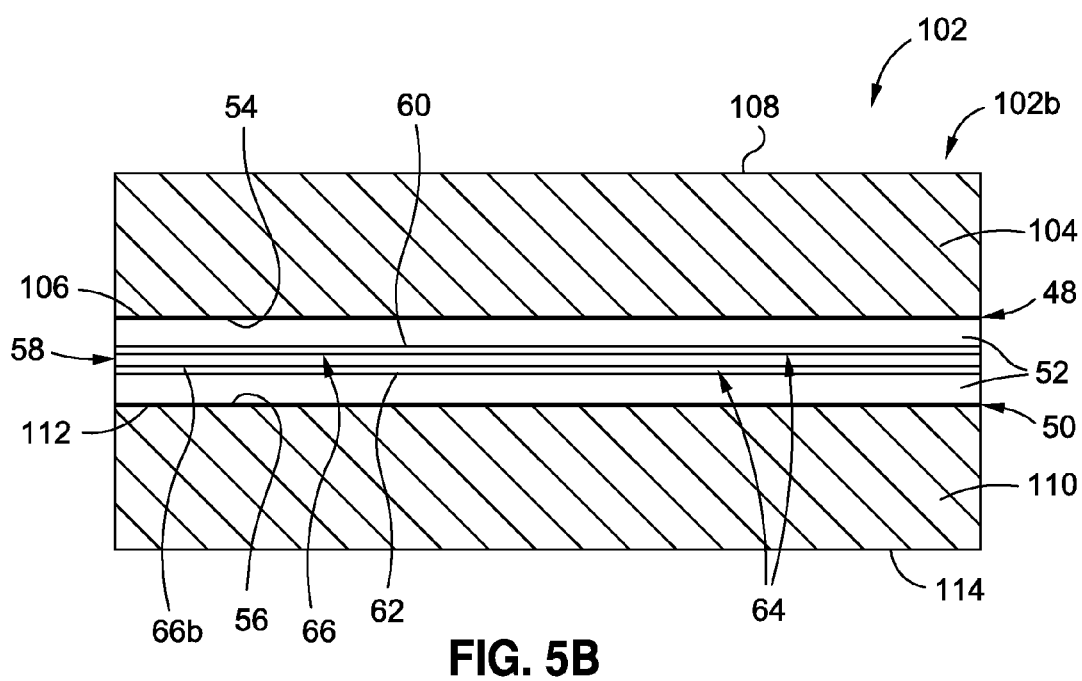
FIG. 5B is an illustration of a partial cross-sectional view of another embodiment of a bonded structure having another one of the embodiments of the electrical sensor network of the disclosure.
Figure 7:
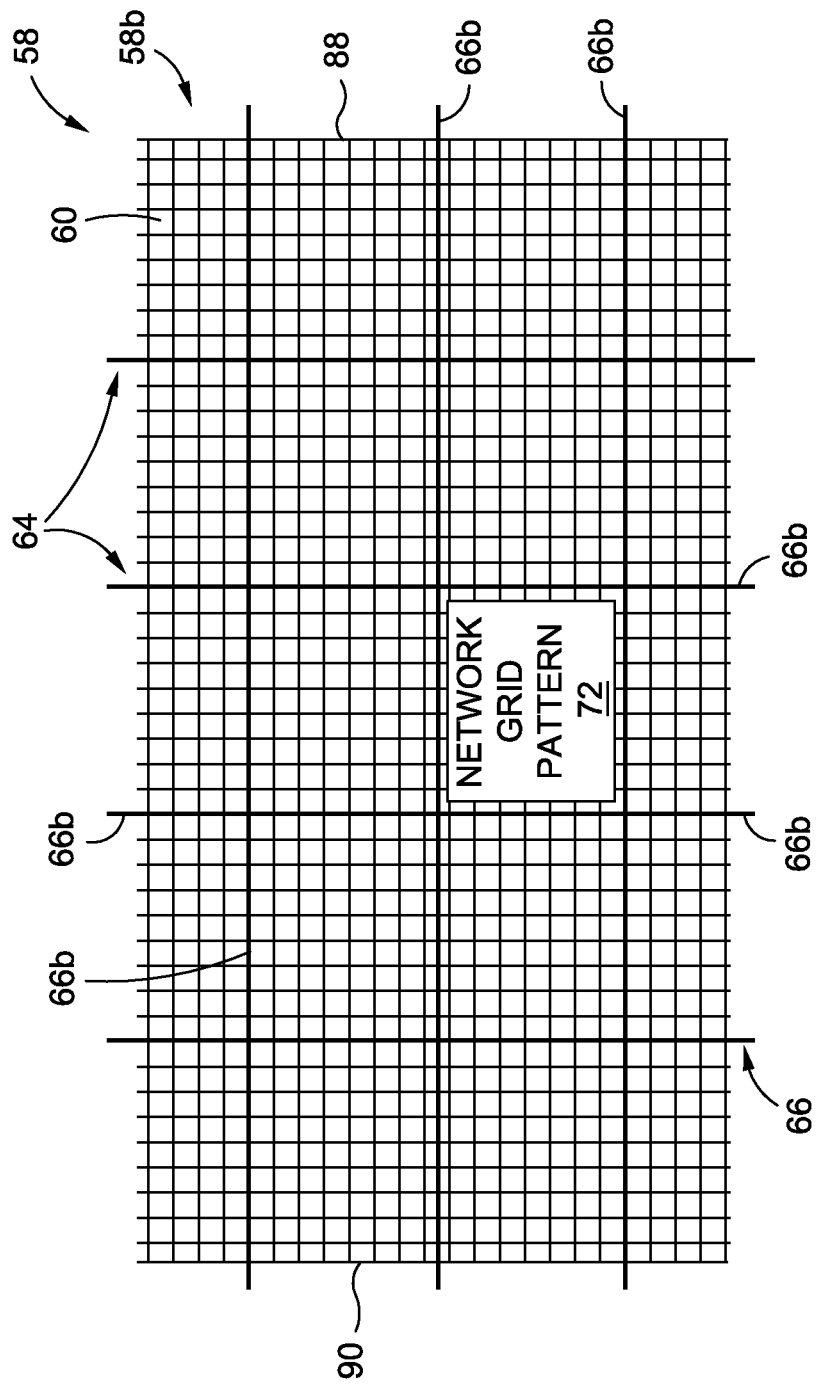
FIG. 7 is an illustration of a top view of another one of the embodiments of a scrim ply layer with sensor fibers.

In another embodiment, sensor elements 66 may be attached or integrated into an existing or known scrim ply layer 58 (see FIG. 7) integrated with the adhesive layer 52. FIG. 7 is an illustration of a top view of another one of the embodiments of the scrim ply layer 58 in the form of a scrim ply layer 58b with an electrical sensor network 64 having sensor elements 66 in the form of active sensor fibers 66b integrated into or attached onto the scrim ply layer 58. As shown in FIG. 7, the sensor fibers 66b form a network grid pattern 72. As shown in FIGS. 5B and 7, the scrim ply layer 58 has a first side 60 (see FIGS. 5B and 7), a second side 62 (see FIG. 5B), a first end 88 (see FIG. 7) and a second end 90 (see FIG. 7).

As shown in FIG. 2, the system 30 further comprises an electrical power source 74 for providing electrical power to the electrical sensor network 64. The electrical power source 74 may comprise batteries, voltage, RFID (radio frequency identification), magnetic induction transmission, or another suitable electrical power source. The electrical power source 74 is preferably wireless.

As shown in FIG. 2, the system 30 further comprises a digital data communications network 76 for retrieving and processing data from the electrical sensor network 64. The digital data communications network 76 is preferably wireless. The digital data communications network 76 may comprise a data retrieval system 78 for retrieving data from the electrical sensor network 64. The data retrieval system 78 may comprise RFID, a radio transceiver (a device that has both a transmitter and a receiver which are combined and share common circuitry or a single housing), or another suitable data retrieval system.

The electrical sensor network 64 monitors adhesive integrity 82 (see FIG. 2) within the cured bondline 32 on demand by interpreting changes in local dynamic responses 84 (see FIG. 2) and electromechanical properties 86 (see FIG. 2) directly measured at or within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline 32 of the bonded structural assembly 34. The integrity of the cured bondline 32 may be determined by interpreting changes in local dynamic responses 84 and electromechanical properties 86 directly measured at or within the cured bondline 32. Additional sensor elements 66, such as fiber optic based materials to assess moisture ingression, piezoelectric sensors to assess strain, or other sensing methods may also be incorporated into the adhesive layer 52. Other functional aspects of the scrim ply layer 58 may also be maintained, including control of bondline thickness, bondline tack control, and/or adhesive uniformity of the bondline.

As shown in FIG. 2, the digital data communications network 76 may further comprise a data processing system 80 for processing data from the electrical sensor network 64. The data processing system 80 may comprise, for example, a known computer processor (not shown), a database (not shown), and a data storage and management system (not shown).

The system 30 monitors adhesive integrity 82 within the cured bondline 32 of the bonded structural assembly 34. Preferably, the system 30 is used for monitoring adhesive integrity at or within the cured bondline 32 of bonded structural assemblies 34, such as bonded structural assemblies for use in aircraft 10 (see FIG. 1), spacecraft, aerospace vehicles, space launch vehicles, rockets, satellites, rotorcraft, watercraft, boats, trains, automobiles, trucks, buses, architectural structures, or other suitable vehicles and structures.

Figure 3:
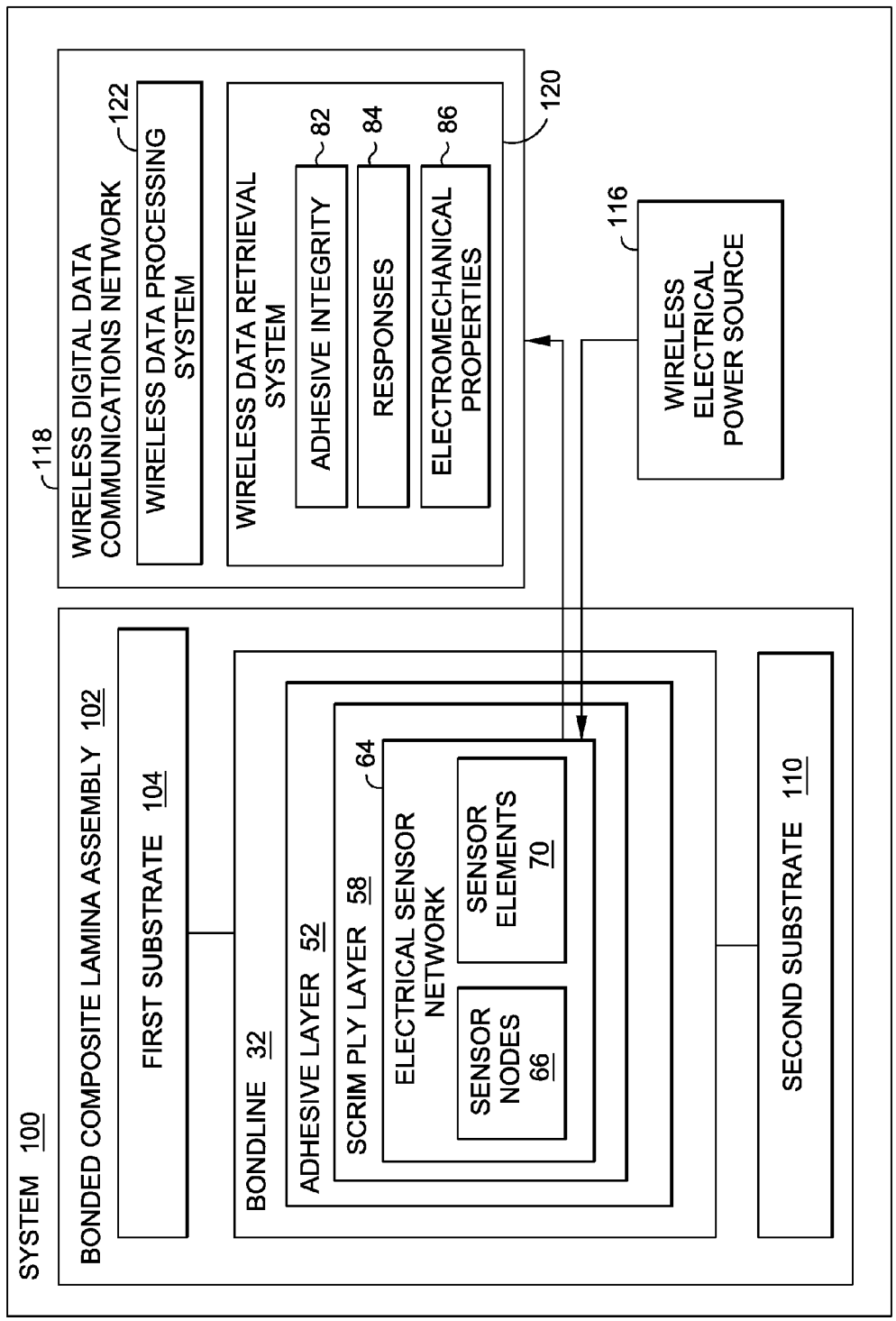
FIG. 3 is an illustration of a block diagram of another one of the embodiments of a system for monitoring adhesive integrity of the disclosure.

FIG. 3 is an illustration of a block diagram of another one of the embodiments of a system 100 for monitoring adhesive integrity within the cured bondline 32 of a bonded composite lamina assembly 102. The system 100 comprises the bonded composite lamina assembly 102 have the cured bondline 32. As shown in FIGS. 5A-5B, the bonded composite lamina assembly 102 may comprise a first substrate 104 and a second substrate 110. The first substrate 104 has a first side 106 and a second side 108. The second substrate 110 has a first side 112 and a second side 114. The first substrate 104 and the second substrate 110 are preferably both made of a composite material comprising polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. FIG. 5A is an illustration of a partial cross-sectional view of an embodiment of a bonded structure 102a having one of the embodiments of the electrical sensor network 64 of the disclosure. As shown in FIG. 5A, the electrical sensor network 64 comprises sensor elements 66 comprising active sensor nodes 66a. FIG. 5B is an illustration of a partial cross-sectional view of another embodiment of a bonded structure 102b having another one of the embodiments of the electrical sensor network 64 of the disclosure. As shown in FIG. 5B, the electrical sensor network 64 comprises sensor elements 66 comprising active sensor fibers 66b.

As shown in FIGS. 5A-5B, the cured bondline 32 of the bonded structural assembly 102 comprises adhesive layer or layers 52. The adhesive layer or layers 52 may comprise an adhesive material such as an epoxy adhesive, a polyurethane adhesive, a toughened acrylic adhesive, or another suitable adhesive. The cured bondline 32 further comprises a scrim ply layer 58 integrated with the adhesive layer or layers 52. As shown in FIG. 5A, the scrim ply layer 58 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 is multifunctional and acts as an adhesive layer by being integrated in the adhesive layer 52 and also acts as a bondline monitoring system. The cured bondline 32 further comprises an electrical sensor network 64 integrated with the scrim ply layer 58. The electrical sensor network 64 preferably comprises a plurality of spaced sensor elements 66 comprising active sensor nodes 66a (see FIG. 5A), active sensor fibers 66b (see FIG. 5B), active sensor wires (not shown), sensor fiber optic wires (not shown), sensor coatings on fibers (not shown), carbon nanotubes (not shown), passive sensors, or another suitable sensor element. The sensor elements 66 preferably have modalities based on ultrasonic wave propagation and electromechanical impedance. The monitoring system 100 provides for an internal electrical sensor network 64 and internal sensor elements 66 at or within the cured bondline 32 to provide for direct measurement and assessment of the bondline characteristics and bondline integrity directly at or within the cured bondline 32 itself.

As shown in FIG. 3, the system 100 further comprises a wireless electrical power source 116 for providing electrical power to the electrical sensor network 64. The wireless electrical power source 74 may comprise batteries, voltage, RFID (radio frequency identification), magnetic induction transmission, or another suitable wireless electrical power source.

As shown in FIG. 3, the system 100 further comprises a wireless digital data communications network 118 for retrieving and processing data from the electrical sensor network 64. The wireless digital data communications network 118 may comprise a wireless data retrieval system 120 for retrieving data from the electrical sensor network 64. The wireless data retrieval system 120 may comprise RFID, a radio transceiver, or another suitable data retrieval system. The electrical sensor network 64 monitors adhesive integrity 82 (see FIG. 3) within the cured bondline 32 on demand by interpreting changes in local dynamic responses 84 (see FIG. 3) and electromechanical properties 86 (see FIG. 3) directly measured within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline 32 and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline 32 of the bonded composite lamina assembly 102. The integrity of the cured bondline 32 may be determined by interpreting changes in local dynamic responses 84 and electromechanical properties 86 directly measured at or within the cured bondline 32. Additional sensor elements 66, such as fiber optic based materials to assess moisture ingression, piezoelectric sensors to assess strain, or other sensing methods may also be incorporated into the adhesive layer 52. Other functional aspects of the scrim ply layer 58 may also be maintained, including control of bondline thickness, bondline tack control, and/or adhesive uniformity of the bondline.

As shown in FIG. 3, the wireless digital data communications network 118 may further comprise a wireless data processing system 122 for processing data from the electrical sensor network 64. The wireless data processing system 122 may comprise, for example, a known a computer processor (not shown), a database (not shown), and a data storage and management system (not shown).

The system 100 monitors adhesive integrity within the cured bondline 32 of the bonded composite lamina assembly 102. Preferably, the system 100 is used for monitoring adhesive integrity within the cured bondline 32 of bonded composite lamina assemblies 102, such as bonded composite lamina assemblies used in aircraft, spacecraft, aerospace vehicles, space launch vehicles, rockets, satellites, rotorcraft, watercraft, boats, trains, automobiles, trucks, buses, architectural structures, or other suitable vehicles and structures.

Figure 8:
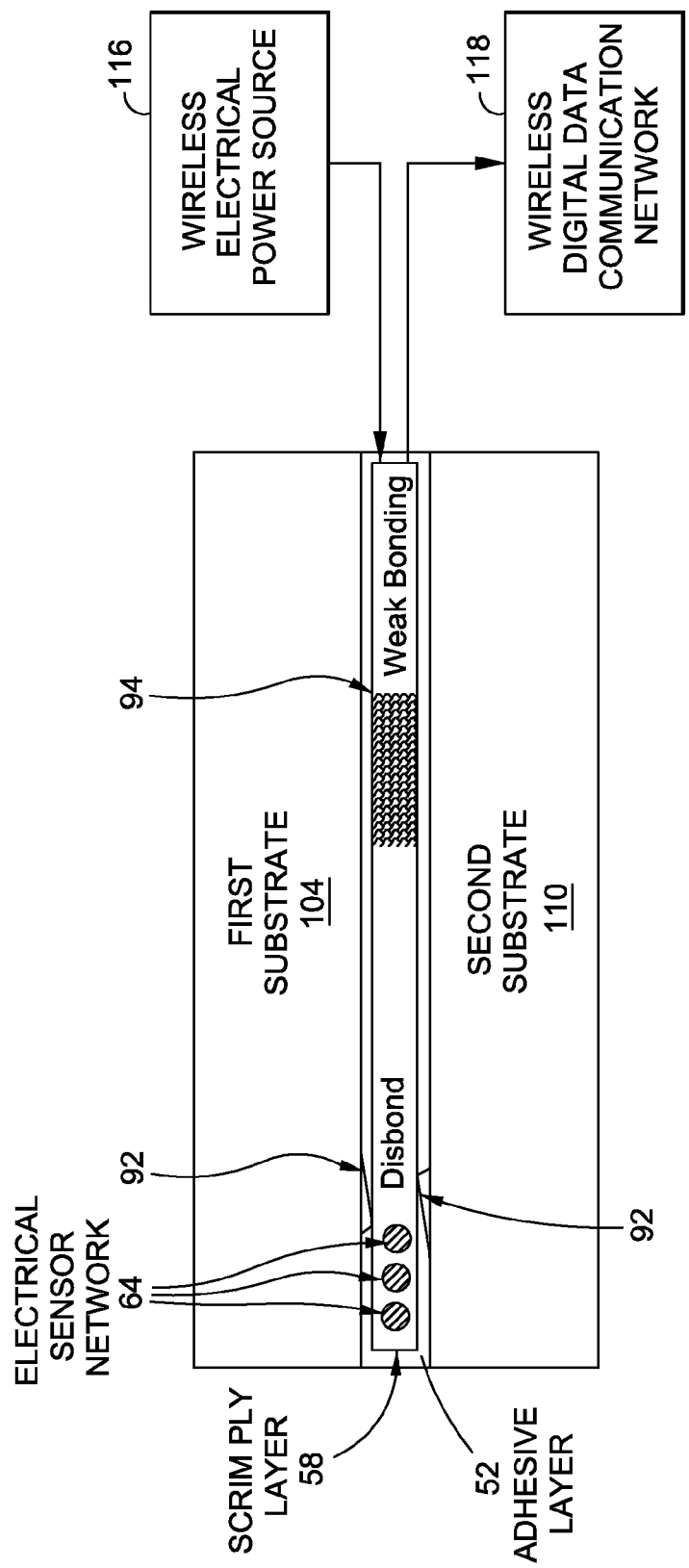
FIG. 8 is an illustration of a schematic diagram of one of the embodiments of a system of the disclosure showing detection of disbonds and weak bonding.

FIG. 8 is an illustration of a schematic diagram of one of the embodiments of the system 100 of the disclosure showing detection of disbonds 92 and weak bonding 94. FIG. 8 shows the first substrate 104 bonded to the second substrate 110 with the scrim ply layer 58 integrated with the adhesive layer 52, and the scrim ply layer 58 having the electrical sensor network 64 integrated with the scrim ply layer 58. The wireless electrical power source 116 provides electrical power to the electrical sensor network 64 of the system 100. The adhesive layer 52 with the scrim ply layer 58 is shown with disbonds 92 and weak bonding 94. The wireless digital data communication network 118 processes the disbond 92 and weak bonding 94 data from the electrical sensor network 64 to monitor the health of the system 100.

Figure 9:
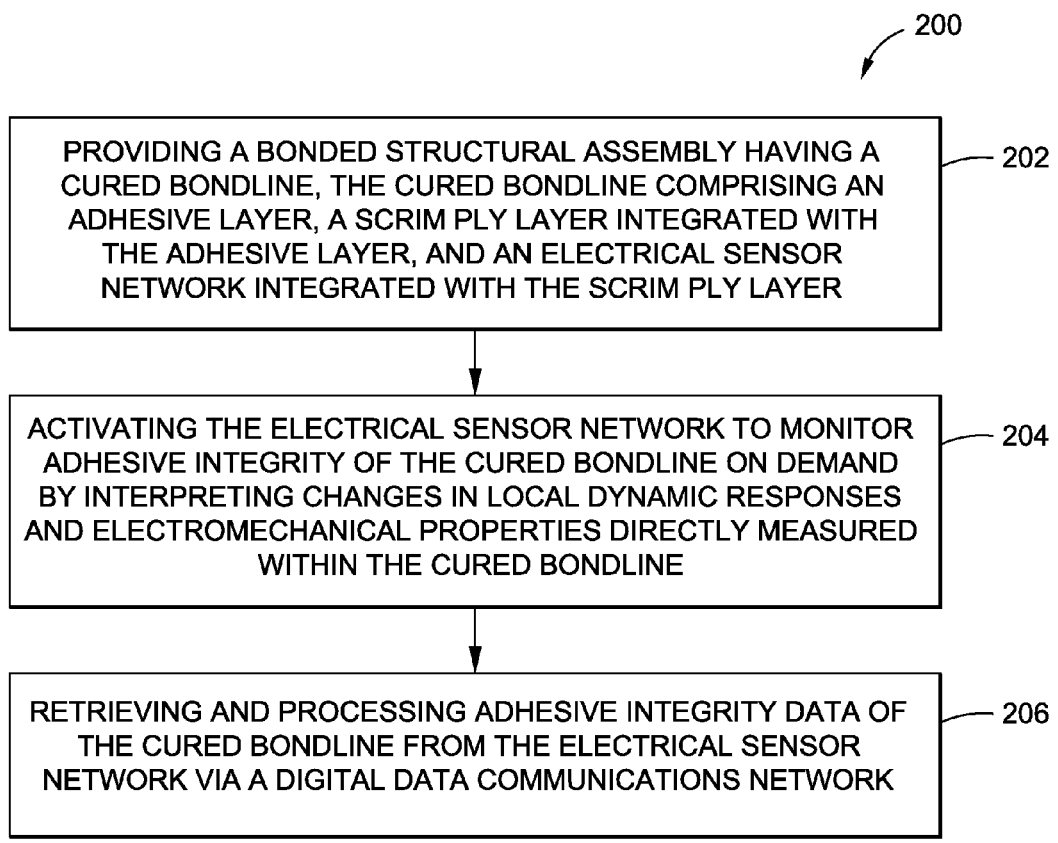
FIG. 9 is an illustration of a flow diagram of an embodiment of a method for monitoring adhesive integrity of the disclosure.

In another embodiment of the disclosure, there is provided a method 200 for monitoring adhesive integrity within a cured bondline 32 (see FIGS. 2, 3) of a bonded structural assembly 34 (see FIG. 2). FIG. 9 is an illustration of a flow diagram of an embodiment of a method 200 for monitoring adhesive integrity within the cured bondline 32. The method 200 comprises step 202 of providing the bonded structural assembly 34 (see FIGS. 4A-4C) having the cured bondline 32. The bonded structural assembly 34 may preferably comprise a bonded composite lamina assembly 102 (see FIG. 3). As discussed above and as shown in FIGS. 4A-4C, the bonded structural assembly 34 may comprise first structure 36 and second structure 42. The first structure 36 may be made of a composite material, a metal material, a combination thereof, or another suitable material. The second structure 36 may be made of a composite material, a metal material, a combination thereof, or another suitable material. Preferably, the composite material for the first structure 36 and/or the second structure 42 comprises polymeric composites, fiber-reinforced composite materials, fiber-reinforced polymers, carbon fiber reinforced plastics (CFRP), glass-reinforced plastics (GRP), thermoplastic composites, thermoset composites, epoxy resin composites, shape memory polymer composites, ceramic matrix composites, or another suitable composite material. Preferably, the metal material for the first structure 36 and/or the second structure 42 comprises aluminum, stainless steel, titanium, alloys thereof, or another suitable metal or metal alloy.

As discussed above, the cured bondline 32 comprises the adhesive layer 52, the scrim ply layer 58 integrated with the adhesive layer 52, and the electrical sensor network 64 integrated with the scrim ply layer 58. As shown in FIG. 4A, the adhesive layer 52 may comprise a first side 54 and a second side 56. As discussed above, the adhesive layer 52 may comprise an adhesive material such as an epoxy adhesive, a polyurethane adhesive, a toughened acrylic adhesive, or another suitable adhesive. As discussed above, the scrim ply layer 58 integrated with the adhesive layer 52 has a first side 60 and a second side 62. The scrim ply layer 58 preferably comprises a material fabricated from various fiber materials, such as nylon fiber material, polyester fiber material, glass fiber material, or another suitable fiber material. The scrim ply layer 58 may be multifunctional and act as an adhesive layer by being integrated in the adhesive layer 52 and may also act as a bondline monitoring system. As discussed above, the electrical sensor network 64 may comprise a plurality of spaced sensor elements 66 comprising active sensor nodes 66a, active sensor fibers 66b, active sensor wires (not shown), sensor fiber optic wires (not shown), sensor coatings on fibers (not shown), carbon nanotubes (not shown), passive sensors, or another suitable sensor element. The passive elements 66 preferably have modalities based on ultrasonic wave propagation and electromechanical impedance. The method 200 provides for an internal electrical sensor network 64 and internal sensor elements 66 at or within the cured bondline 32 to provide for direct measurement and assessment of the bondline characteristics and bondline integrity directly at or within the cured bondline 32 itself.

As shown in FIG. 9, the method 200 further comprises step 204 of activating the electrical sensor network 64 (see FIGS. 4A-4C) to monitor adhesive integrity 82 of the cured bondline 32 on demand by interpreting changes in local dynamic responses 84 and electromechanical properties 86 (see FIG. 2) directly measured within the cured bondline 32. Preferably, the electrical sensor network 64 is activated with an electrical power source 74 (see FIG. 2), and more preferably, with a wireless electrical power source 116 (see FIG. 3). The electrical power source 74 or wireless electrical power source 116 may comprise batteries, voltage, RFID (radio frequency identification), magnetic induction transmission, or another suitable wireless electrical power source.

As shown in FIG. 9, the method 200 further comprises step 206 of retrieving and processing adhesive integrity data of the cured bondline 32 from the electrical sensor network 64 via the digital data communications network 76 (see FIG. 2). Preferably, the digital data communications network is a wireless digital data communications network 118 (see FIG. 3). The digital data communications network 76 may comprise a data retrieval system 78 for retrieving data from the electrical sensor network 64. The data retrieval system 78 may comprise RFID, a radio transceiver, or another suitable data retrieval system. The wireless digital data communications network 118 may comprise a wireless data retrieval system 120 for retrieving data from the electrical sensor network 64. The electrical sensor network 64 monitors adhesive integrity 82 (see FIGS. 2, 3) within the cured bondline 32 on demand by interpreting changes in local dynamic responses 84 (see FIGS. 2, 3) and electromechanical properties 86 (see FIGS. 2, 3) directly measured within the cured bondline 32. The electrical sensor network 64 may also continuously monitor the adhesive integrity 82 within the cured bondline 32. The local dynamic responses 84 and the electromechanical properties 86 are preferably directly measured at or within the cured bondline 32 and may comprise disbonds 92 (see FIG. 8), weak bonding 94 (see FIG. 8), strain levels, moisture ingression, materials change, cracks, voids, delamination, porosity, or other suitable local dynamic responses or electromechanical properties or other irregularities which may adversely affect the performance of the cured bondline of the bonded structural assembly. The integrity of the cured bondline 32 may be determined by interpreting changes in local dynamic responses 84 and electromechanical properties 86 directly measured at or within the cured bondline 32.

The digital data communications network 76 may further comprise a data processing system 80 for processing data from the electrical sensor network 64. The wireless digital data communications network 118 may further comprise a wireless data processing system 122 for processing data from the electrical sensor network 64. The data processing system 80 and the wireless data processing system 122 may comprise, for example, a known computer processor (not shown), a database (not shown), and a data storage and management system (not shown).

The method 200 monitors adhesive integrity within the cured bondline 32 of the bonded structural assembly 34, and preferably, monitors adhesive integrity within the cured bondline 32 of the bonded composite lamina assembly 102. Preferably, the method 200 is used for monitoring adhesive integrity within the cured bondline 32 of bonded structural assemblies 34, preferably bonded composite lamina assemblies 102, such as used in aircraft, spacecraft, aerospace vehicles, space launch vehicles, satellites, rotorcraft, watercraft, boats, trains, automobiles, trucks, buses, architectural structures, or other suitable vehicles and structures.

Embodiments of the monitoring systems 30, 100 and monitoring method 200 provide for the integration of active sensing materials into an adhesive scrim ply layer 58 to create a multifunctional system or matrix capable of serving as both an adhesive layer and a bondline monitoring system. The sensor elements 66 integrated into the adhesive scrim ply layer 58 matrix interpret changes within the local dynamic responses 84 and the electromechanical properties 86 measured within the bondline interface, and the sensor elements 66 may assess key characteristics such as disbonds, strain levels, moisture ingression, materials changes, cracks, voids, delamination, porosity, and/or other key characteristics at or within the cured bondline interface. Embodiments of the monitoring systems 30, 100 and monitoring method 200 may utilize various sets of active sensor elements 66, such as sensing materials with modalities based on ultrasonic wave propagation and electromechanical impedance based on the scrim meshing pattern, to perform as a power and information network. Activation of the system and data retrieval may be performed wirelessly using a wireless electrical power source 116, a wireless data retrieval system 120, and a wireless data processing system 122 for interpretation of data in situ at the cured bondline 32 of the structural assembly such as the bonded composite lamina assembly 102. Embodiments of the monitoring systems 30, 100 and monitoring method 200 provide a cured bondline 32 with an embedded multifunctional scrim ply layer 58 to monitor on demand or continuously for a change in the bondline interface adhesive integrity quality during both manufacturing and in-service. Such cured bondlines or bonded joints may reduce the overall weight of the structures and structural components by reducing the volume of heavy joints based on the use of fasteners. Bonded joints accomplish this, in part, by spreading the load over a larger footprint.

Embodiments of the monitoring systems 30, 100 and monitoring method 200 may provide monitoring of adhesive integrity at or within the cured bondline 32 in bonded structural assemblies used in aircraft, spacecraft, aerospace vehicles, space launch vehicles, rockets, satellites, rotorcraft, watercraft, boats, trains, automobiles, trucks, buses, and other suitable transport vehicles and structures. Embodiments of the monitoring systems 30, 100 and monitoring method 200 may provide in situ non-destructive systems and method for characterizing bonding properties and ensuring the bondline integrity of structurally bonded parts continuously throughout the service lifetime of the hardware and structurally bonded parts.

Embodiments of the monitoring systems 30, 100 and monitoring method 200 have the ability to interrogate the cured bondline while the structure or structural component parts are in-service; may decrease costs and flow time to the process of assuring bondline integrity; may be carried out on demand on a real time basis or continuously on a real time basis so that the information about the bondline integrity is available at all times; and, may predict and monitor the integrity, health and fitness of cured bondlines or bonded joints located remotely, interior, or beneath the structural surface without having to disassemble or remove structures or structural components or drill holes into the structures or structural components for insertion of any measurement tools. Moreover, embodiments of the monitoring systems 30, 100 and monitoring method 200 may provide for an internal electrical sensor network and internal sensors at or within the cured bondline to provide for direct measurement and assessment of the bondline characteristics and bondline integrity directly at or within the bondline itself. Finally, embodiments of the monitoring systems 30, 100 and monitoring method 200 may be used to predict deterioration or weaknesses directly at or within the cured bondline or bonded joint prior to the actual development of such deterioration or weaknesses, and thus, may increase reliability of the structure or structural component parts, may increase the safety of the adhesive bondline, and may reduce overall manufacturing and maintenance costs over the life of the structure or structural component parts.

Figure 10:
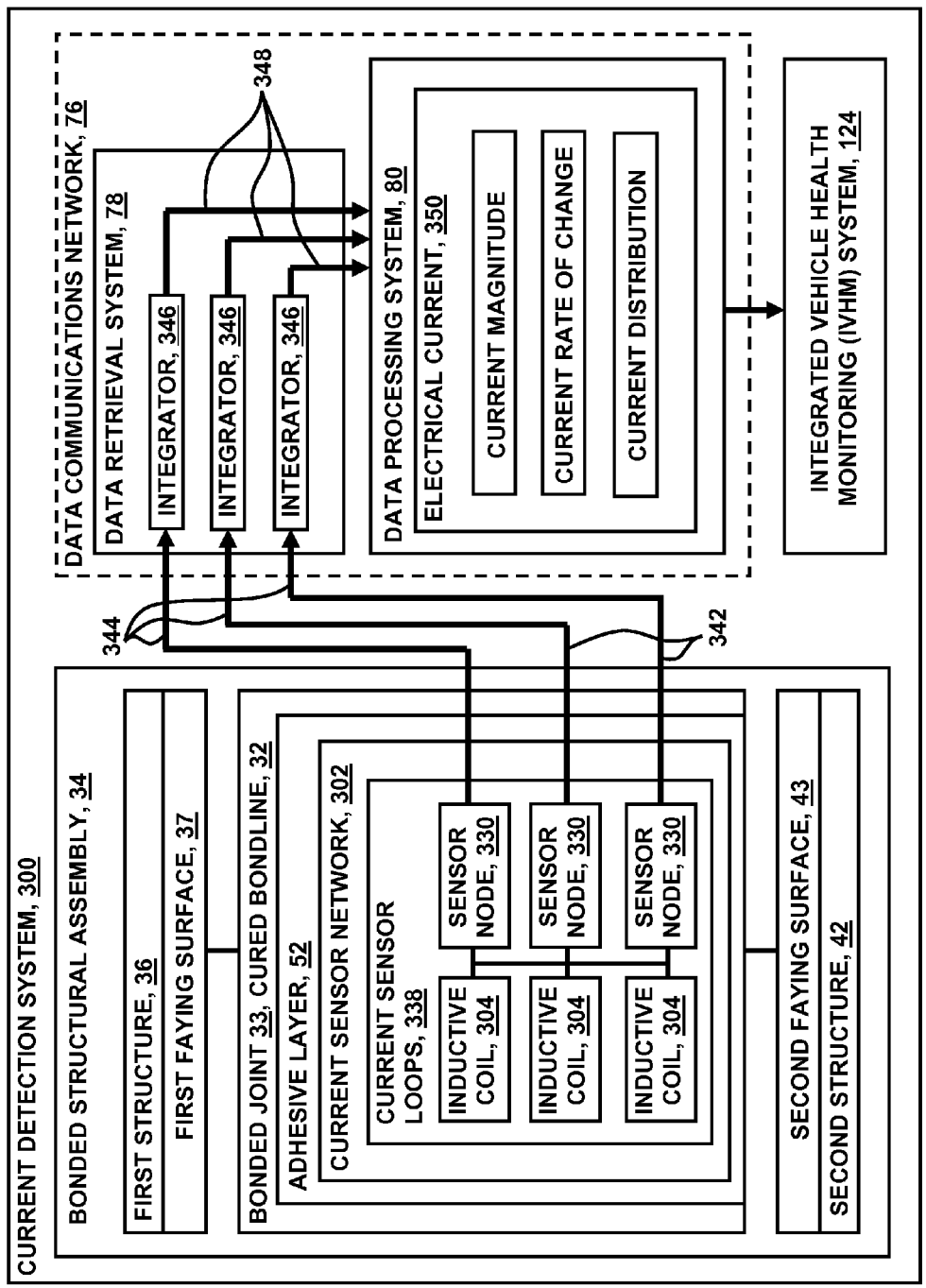
FIG. 10 is an illustration of a block diagram of an embodiment of a system for detecting and monitoring electrical current flow through a bonded joint.

FIG. 10 shows a block diagram of an embodiment of a current detection system 300 for detecting and monitoring electrical current 350 (FIG. 11) flow through a bonded joint 33 of a bonded structural assembly 34. As indicated above, the bonded structural assembly 34 may include a first structure 36 and a second structure 42. The first structure 36 and/or the second structure 42 may be formed of composite material such as fiber-reinforced polymer matrix material. However, the first structure 36 and/or the second structure 42 may be formed of metallic material, ceramic material, or a combination of composite material, ceramic material, and metallic material. The first structure 36 has a first faying surface 37 and the second structure 42 has a second faying surface 43. The first and second faying surfaces 37, 43 may be bonded together by an adhesive layer 52 of a cured bondline 32 located between the first faying surface 37 and the second faying surface 43. As mentioned above, the adhesive layer 52 may be formed of a material selected from the group comprising epoxy adhesives, polyurethane adhesives, and acrylic adhesives, or any other type of structural adhesive. In some examples, the structural assembly 34 may be configured with no mechanical fasteners in the bonded joint 33. However, in other examples, one or more mechanical fasteners (not shown) or other mechanical features may be included in the bonded joint 33 to mechanically assist in coupling the first structure 36 to the second structure 42.

Figure 11:
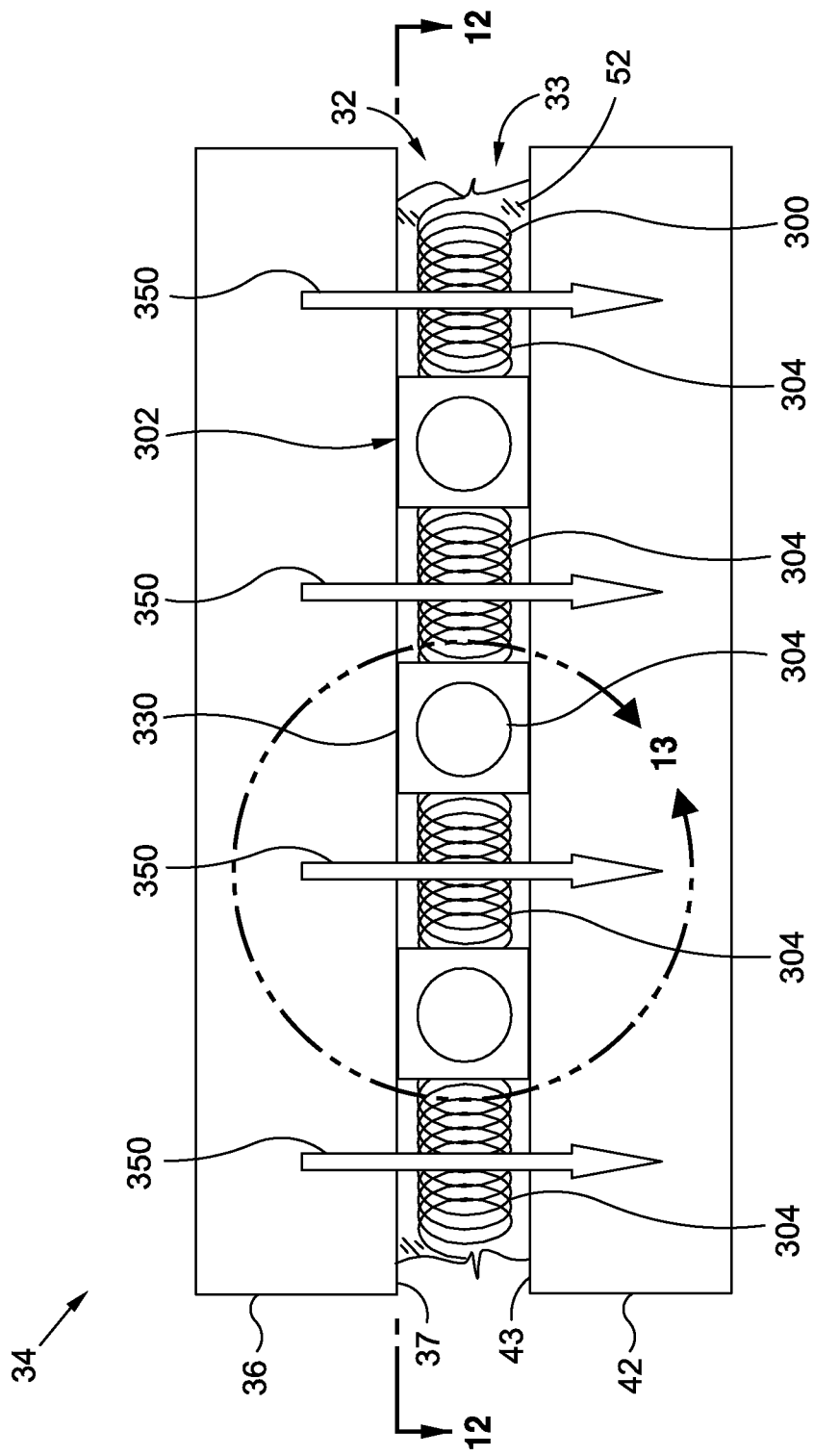
FIG. 11 is an illustration of a partial cross-sectional view of a structural assembly showing an embodiment of a current sensor network embedded in an adhesive layer of a bonded joint joining the first and second structure of the structural assembly.

In FIG. 10, the current detection system 300 may further include a current sensor network 302 that may be embedded in the adhesive layer 52 of the cured bondline 32 of the structural assembly 34. In an example, the current sensor network 302 may include a plurality of inductive coils 304 and a plurality of current sensor nodes 330 electrically interconnecting the inductive coils 304. In the example shown, the inductive coils 304 and the current sensor nodes 330 may be arranged to form a plurality of current sensor loops 338 (FIG. 11). As described in greater detail below, an electrical current 350 flowing or passing through the adhesive layer 52 may have a magnetic field 352 (FIG. 11) associated with the electrical current 350. The electrical current 350 passing through the adhesive layer 52 may be described as a transient current or a current pulse passing through the adhesive layer 52 along a direction from the first structure 36 to the second structure 42, or vice versa. The electrical current 350 flowing through the adhesive layer 52 may be the result of a lighting strike or other electrical charge applied to the structural assembly 34 or flowing into the structural assembly 34 from another location on a vehicle or structure containing the structural assembly 34.

Induced current 306 (FIG. 13) may be generated in the inductive coils 304 of the current sensor loops 338 when electrical current 350 is flowing through the adhesive layer 52. The induced current 306 may be generated as a result of the magnetic field 352 associated with the electrical current 350 through the adhesive layer 52. The magnetic field 352 may induce a relatively low-magnitude induced current 306 in the inductive coils 304. For example, the induced current 306 may be on the order of microamps or milliamps, and may be generated in response to an electrical current 350 passing through the adhesive layer 52 on the order of from 100 milliamps up to 100 amps or more. For example, electrical current 350 passing through a structural assembly 34 as a result of a lightning strike may be on the order of up to 100,000 amps or more, and may be associated with a voltage of up to 100 kilovolts or more.

In FIG. 10, the current detection system 300 may further include a digital data communications network 76 which may be located external to the cured bondline 32. The digital data communications network 76 may be coupled to the current sensor nodes 330 by one or more signal wires 342. The digital data communications network 76 may receive and process current signals 344 which may be generated by electronic circuitry (not shown) included in the current sensor nodes 330. The current signals 344 may be representative of the induced current 306. For example, the current signal 344 generated by a given current sensor node 330 may be proportional to the magnitude of the induced current 306 in one or more of the inductive coils 304 that are electrically connected to the given current sensor node 330. In some examples, the current signal 344 generated by a given current sensor node 330 may be proportional to the local magnitude (e.g., amperage) of the electrical current 350 passing through the adhesive layer 52 at a location adjacent to the given current sensor node 330. In this regard, the magnitude of the induced current 306 in the inductive coils 304 embedded throughout the adhesive layer 52 may be different at different locations of the adhesive layer 52, as described in greater detail below.

The digital data communications network 76 may use the current signals 344 to detect and monitor electrical current 350 passing through one or more portions of the cured bondline 32. In some examples, the digital data communications network 76 may include a data retrieval system 78 for receiving current signals 344 from the current sensor nodes 330. The data retrieval system 78 may include one or more current integrators 346. The current integrators 346 may be electrically connected to the current sensor nodes 330. In some examples, each one of the current sensor nodes 330 may be electrically connected to a dedicated current integrator 346. A current integrator 346 may integrate the induced current 306 over time and may generate an output signal 348 which may be proportional to the magnitude of the current signal 344 received by the current integrator 346.

The digital data communications network 76 may further include a data processing system 80 which may receive the output signals 348 from the data retrieval system 78. As indicated above, the data retrieval system 78 and data processing system 80 may comprise, for example, a known computer processor (not shown), a database (not shown), and/or a data storage and management system (not shown). The data processing system 80 may process the output signals 348 to detect, monitor, and/or characterize one or more parameters associated with the electrical current 350 passing through the adhesive layer 52. For example, the digital data communications network 76 may detect the existence of electrical current 350 passing through the cured bondline 32 by comparing the magnitude of the electrical current 350 to a predetermined threshold current value. In other examples, the digital data communications network 76 may characterize the electrical current 350 passing through the adhesive layer 52 by summing the current signals 344 from one or more of the current integrators 346 to determine the total electrical charge of the electrical current 350 passing through the cured bondline 32. The digital data communications network 76 may also characterize the electrical current 350 passing through the adhesive layer 52 by determining the event time (e.g., total elapsed time) during which the electrical current 350 passes through the adhesive layer 52, and/or determining the rate of change of the electrical current 350 as it passes through the adhesive layer 52. In some examples, the digital data communications network 76 may convert the current signals 344 to voltage signals (not shown), and may interpret or analyze the voltage signals to detect, monitor, and/or characterize the electrical current 350 passing through the cured bondline 32.

In FIG. 10, the current detection system 300 may be in communication with an integrated vehicle health management (IVHM) system 124 as may be included in a vehicle such as an aircraft. The digital data communications network 76 may be configured to communicate or transmit the electrical current 350 data to an IVHM system 124 which may, in turn, communicate the electrical current 350 data to an external maintenance tracking system (not shown) and/or to appropriate maintenance personnel to monitor and/or assess the potential need for inspection of one or more bonded joints 33 that may have been subjected to relatively high-intensity electrical current 350 flow as detected by the current detection system 300. For example, a vehicle such as an aircraft 10 (FIG. 1) may include a plurality of bonded structural assemblies 34 each including one or more bonded joints 33. The bonded joints 33 may include one or more cured bondlines 32 incorporating a current sensor network 302 embedded in an adhesive layer 52 of the cured bondline 32. The current sensor network 302 in the cured bondline 32 of the different bonded structural assemblies 34 may be in communication with an IVHM system 124. The IVHM system 124 may monitor the electrical current 350 passing through each cured bondline 32 of the bonded structural assemblies 34. In the event that one or more of the bonded structural assemblies 34 are subjected to a transient electrical charge such as due to a lightning strike on an aircraft, the IVHM system 124 may determine the magnitude of the lightning-induced electrical charge passing through one or more of the bonded joints 33 at different location in the aircraft 10. In some examples, the IVHM system 124 may record a time-history of the electrical charges passing through different bonded joints 33 of the aircraft 10 to establish a propagation or flow direction or path of the lightning-induced electrical charge as it passes throughout the aircraft 10.

FIG. 11 shows a cross-sectional view of a structural assembly 34 of a first structure 36 adhesively bonded to a second structure 42 at a bonded joint 33. The bonded joint 33 includes a cured bondline 32 contain adhesive bonding the first faying surface 37 of the first structure 36 to the second faying surface 43 of the second structure 42. The cured bondline 32 includes a current sensor network 302 embedded in the adhesive layer 52 of the bonded joint 33. The current sensor network 302 includes a plurality of inductive coils 304 embedded in the adhesive layer 52 and electrically interconnected to one another by a plurality of current sensor nodes 330. Each one of the inductive coils 304 has a lengthwise direction oriented generally parallel to the first and second faying surfaces 37, 43 of the first and second structure 36, 42. An electrical current 350 is shown passing through the adhesive layer 52 along a direction from the first structure 36 to the second structure 42. However, as indicated above, the electrical current 350 may pass through the adhesive layer 52 along a direction from the second structure 42 to the first structure 36. A magnetic field 352 may be associated with the electrical current 350 passing through the adhesive layer 52. As indicated above, the magnetic field 352 may induce an induced current 306 in the inductive coils 304 which may be picked up at the current sensor nodes 330. The current sensor nodes 330 may generate current signals 344 representative of the induced current 306. The current signals 344 may be transmitted via signal wires 342 to the digital data communications network 76 as shown in FIG. 1 and described above.

Figure 12:
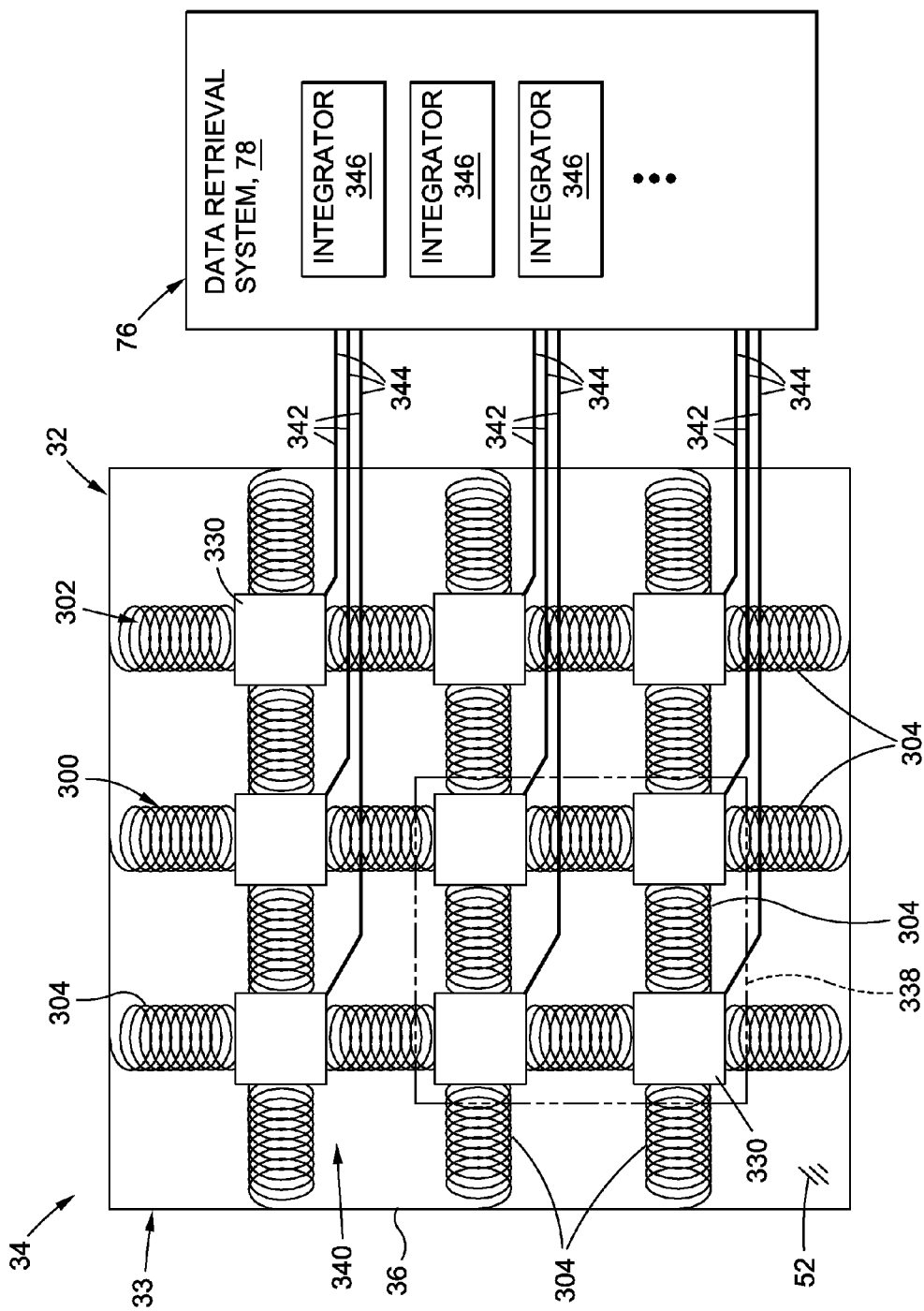
FIG. 12 is an illustration of the top view of an embodiment of a current sensor network as may be embedded in an adhesive layer of the bonded joint.

FIG. 12 shows a top view of an embodiment of a current sensor network 302 as may be embedded in an adhesive layer 52 of a bonded joint 33. In the example shown, the current sensor network 302 is comprised of a plurality of relatively straight sections of inductive coils 304 embedded in the adhesive layer 52. One or more of the inductive coils 304 may be generally straight. One or both of the opposing ends of the inductive coil 304 may be electrically connected to a current sensor node 330. As indicated above, the current sensor network 302 may include a plurality of current sensor nodes 330. Each one of the current sensor nodes 330 may electrically connect two or more inductive coils 304. In this regard, the current sensor nodes 330 may electrically interconnect the inductive coils 304 to form a plurality of current sensor loops 338.

In FIG. 12, the inductive coils 304 and current sensor nodes 330 may be configured such that current sensor loops 338 are arranged in a generally uniformly-spaced grid pattern 340 within the adhesive layer 52 of the cured bondline 32. However, the inductive coils 304 and the current sensor nodes 330 may be arranged in a non-uniform grid pattern 340 (not shown), or in a combination of a non-uniform grid pattern in some portions of the current sensor network 302, and in a uniform grid pattern 340 in other portions of the current sensor network 302. A generally uniform grid pattern 340 of the inductive coils 304 and current sensor nodes 330 along at least a portion of the cured bondline 32 may allow for sensing electrical current 350 at uniformly-spaced locations defined by the grid pattern 340. In this manner, the magnitude of current signals 344 generated at each one of the current sensor nodes 330 relative to one another may be used to determine the mapping or distribution (e.g., the relative magnitude or amperage) of the electrical current 350 at different locations along the length and width of the cured bondline 32. The spacings between current sensor nodes 330 may be selected based upon the desired fidelity with which the distribution of electrical current 350 may be mapped within the cured bondline 32. For example, the current sensor nodes 330 may be spaced apart at spacings of up to 1 inch or more.

Referring still to FIG. 12, at least some of the inductive coils 304 of the current sensor network 302 may be oriented generally orthogonally relative to one another when the current sensor network 302 is viewed along a direction normal to the first and second faying surfaces 37, 43. In such an arrangement, at least one of the current sensor loops 338 may have a generally square shape defined by an inductive coil 304 on each of four sides of the square-shaped current sensor loop 338 and a current sensor node 330 at each corner of the square-shaped current sensor loop 338 as shown in FIG. 12. However, the inductive coils 304 may be arranged in various orientations to provide any one of a variety of different geometrical shapes of the current sensor loops 338. For example, one or more of the inductive coils 304 of a current sensor network 302 may be provided in non-orthogonal arrangements such as to form a grid pattern 340 of triangularly-shaped current sensor loops (not shown) having an inductive coil 304 on three sides and a current sensor node 330 at each vertex of the triangularly-shaped current sensor loops. In addition, the inductive coils 304 are not limited to being provided in a straight shape extending between a pair of current sensor nodes 330. In this regard, one or more of the inductive coils 304 may be provided in a curved shape, or a combination of a curved shape and a straight shape, when the current sensor network 302 is viewed along a direction normal to the first and second faying surface 37, 43s.

Advantageously, the arrangement of the current sensor loops 338 results in the inducement of generally low-amperage induced current 306 in the inductive coils 304 in response to the magnetic field 352 associated with electrical current 350 passing through the adhesive layer 52 from the first structure 36 to the second structure 42, or vice versa. The current sensor loops 338 may advantageously be immune to electromagnetic interference and/or current from another source flowing through external structure (not shown) located adjacent to the first structure 36 and second structure 42. For example, the current sensor network 302 may be immune to current flow through adjacent skin panels or other structure that may be attached to the first structure 36 and/or the second structure 42.

In FIG. 12, the current sensor network 302 may be connected to a data retrieval system 78 of a digital data communications network 76 (FIG. 1). The data retrieval system 78 may be located external to the cured bondline 32 and may receive current signals 344 via signal wires 342 extending through the adhesive layer 52 from the current sensor nodes 330 to one or more external current integrators 346 of the data retrieval system 78. As indicated above, the current integrators 346 may integrate the current signals 344 over time and generate an output signal 348 which may be proportional to the magnitude of the current signal 344 received by the current integrator 346. The output signals 348 may be transmitted to an external data processing system 80 (FIG. 1) for processing the output signals 348 and determining one or more parameters associated with the electrical current 350 passing through the cured bondline 32. In some examples, the current integrators 346 may integrate the induced currents 306 over time and convert the electrical current 350 signal from an analog signal to a digital signal for processing into an electrical current profile (e.g., rate of change of current (I) flow over time (t), dI/dt) associated with the electrical charge passing through the adhesive layer 52 at a location adjacent to a given current sensor node 330.

Figure 13:
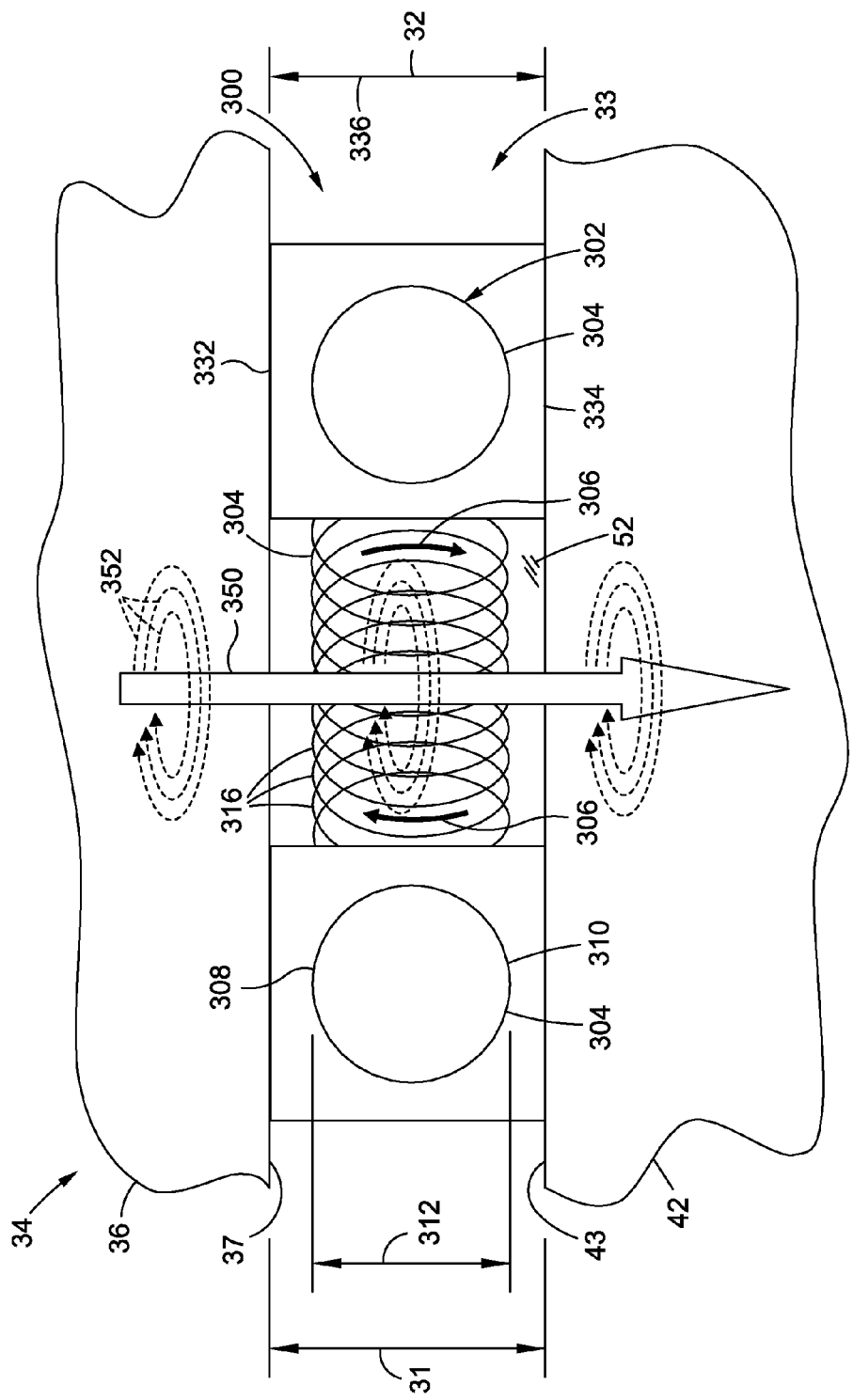
FIG. 13 is an illustration of a partial cross-sectional view of an inductive coil extending between a pair of current sensor nodes of the current sensor network and further illustrating an electrical current passing through the adhesive layer and a magnetic field associated with the electrical current and inducing an induced current in the inductive coil.

FIG. 13 shows a partial cross-sectional view of an inductive coil 304 extending between a pair of current sensor nodes 330 of a current sensor network 302 and further illustrating an electrical current 350 passing through the adhesive layer 52 from the first structure 36 to the second structure 42. Also shown is a magnetic field 352 associated with the electrical current 350. As indicated above, the magnetic field 352 may induce an induced current 306 in the inductive coil 304, and which may be picked up at the current sensor nodes 330 and transmitted in the form of current signals 344 to an external digital data communications network 76 (FIG. 1) configured to process the current signals 344 and detect, analyze, and/or characterize the electrical current 350 passing through the adhesive layer 52 of the cured bondline 32. Alternatively, in an embodiment not shown, one or more of the current sensor nodes 330 may include a current integrator 346 which may generate an output signal 348 based on the induced current 306 in the inductive coils 304. The output signal 348 may then be transmitted via one or more signal wires 342 (FIG. 12) to an external data processing system 80 (FIG. 1).

In FIG. 13, the current sensor network 302 may be provided in a relatively small height enabling the current sensor network 302 to be embedded in relatively thin bondlines of structurally bonded joints 33. In one example, the current sensor network 302 may be sized and configured to fit within a bondline thickness 31 of a cured bondline 32 of no greater than approximately 0.020 inch. The adhesive layer 52 may have an adhesive layer 52 thickness that may be substantially equivalent to the bondline thickness 31. In some examples, the current sensor network 302 may be sized and configured to fit within a bondline thickness 31 of no greater than 0.010 inch or less. In this regard, the inductive coils 304 may be provided in an inductive coil height 312 of no greater than approximately 0.020 inch, and more preferably, in an inductive coil height 312 of no greater than approximately 0.010 inch. Likewise, the current sensor nodes 330 may be provided in a node height 336 of no greater than approximately 0.020 inch and, more preferably, 0.010 inch or less. However, in some examples, the adhesive layer 52 may have a bondline thickness 31 of greater than to a 0.020 inch, which may allow for an increased thickness of the current sensor network 302. In this regard, the inductive coil height 312 and/or the node height 336 may be up 0.030 inch or more.

The inductive coil height 312 of an inductive coil 304 may be defined as the distance between a coil upper side 308 and a coil lower side 310. In some examples, the current sensor network 302 may be configured such that the coil upper side 308 and/or the coil lower side 310 are positioned in non-contacting relation with the first faying surface 37 and/or the second faying surface 43 when the inductive coil 304 is embedded within the adhesive layer 52. The coil upper side 308 and/or the coil lower side 310 may be separated from the first faying surface 37 and/or the second faying surface 43 by a thin layer of adhesive. However, in other examples, the coil upper side 308 and/or the coil lower side 310 may contact the first faying surface 37 and/or the second faying surface 43. In some examples, one or more of the current sensor nodes 330 may be provided in a node height 336 that is substantially equivalent to the desired bondline thickness 31 such that a node upper side 332 and/or a node lower side 334 of at least one current sensor node 330 is in abutting contact with the first faying surface 37 and the second faying surface 43. However, in other examples, one or more of the current sensor nodes 330 may be provided in a node height 336 that is less than the bondline thickness 31 such that a node upper side 332 and/or a node lower side 334 of one or more of the current sensor nodes 330 may be in non-contacting relation to the first faying surface 37 and/or the second faying surface 43. For example, the node upper side 332 and/or the node lower side 334 may be separated from the first faying surface 37 and/or the second faying surface 43 by a thin layer of adhesive.

Each inductive coil 304 may be configured as a generally helically-shaped wire formed as a series of connected 360-degree turns 316. The turns 316 in an inductive coil 304 may be in non-contacting relation to one another and/or may be physically separated and electrically insulated from one another by the adhesive layer 52 within which the inductive coil 304 is embedded. The wire of the inductive coils 304 may have a relative small size (e.g., less than 0.0003 inch diameter) and may be formed of a conductive material such as a metallic material. For example, the inductive coils 304 may be formed of a copper alloy such as copper-nickel, copper-silver, or the inductive coils 304 may be formed of stainless steel, carbon steel, titanium, and other metal alloys or combinations thereof. In some examples, the wires of the inductive coils 304 may be coated with Kapton™ to withstand the high current environment to which a bonded joint 33 may be subjected. The inductive coils 304 of a current sensor network 302 may be substantially similar in geometry, size, and material. However, different portions of a current sensor network 302 may include inductive coils 304 having a different geometry, size, and/or material.

Figure 14:
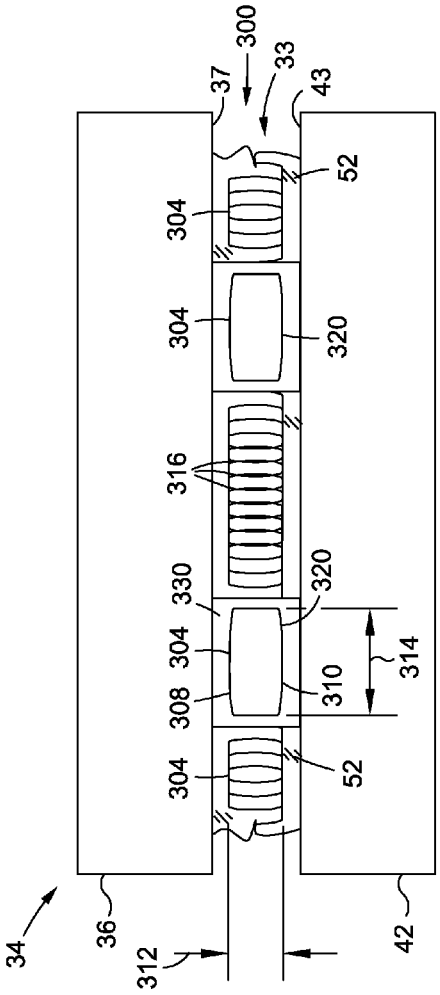
FIG. 14 is an illustration of a partial cross-sectional view of a further embodiment of the current sensor network wherein the inductive coils have a rectangular cross-sectional shape.

FIG. 14 shows a partial cross-sectional view of an embodiment of a current sensor network 302 wherein the inductive coils 304 have a flattened cross-sectional shape 318 configured as a generally rectangular cross-sectional shape 320 when the inductive coils 304 are viewed from an end of the inductive coil 304 along a lengthwise direction of the inductive coil 304. In this regard, the flattened cross-sectional shape 318 of the inductive coil 304 may result in an inductive coil height 312 that is less than an inductive coil width 314, and is in contrast to the circular cross-sectional shape of the inductive coils 304 having a substantially equivalent inductive coil height 312 and width as shown in FIGS. 11 and 13. Advantageously, a flattened cross-sectional shape 318 of the inductive coil 304 may allow for increased cross-sectional area of the inductive coil 304 while reducing the overall height of the inductive coil 304 to fit within a relative small bondline thickness 31. Increasing the cross-sectional area of the inductive coil 304 by providing the inductive coil 304 in a flattened cross-sectional shape 318 may enhance the ability of the inductive coil 304 to pick up a magnetic field 352, and thereby generate an induced current 306 in response to the magnetic field 352 associated with the electrical current 350 passing through the adhesive layer 52.

Figure 15:
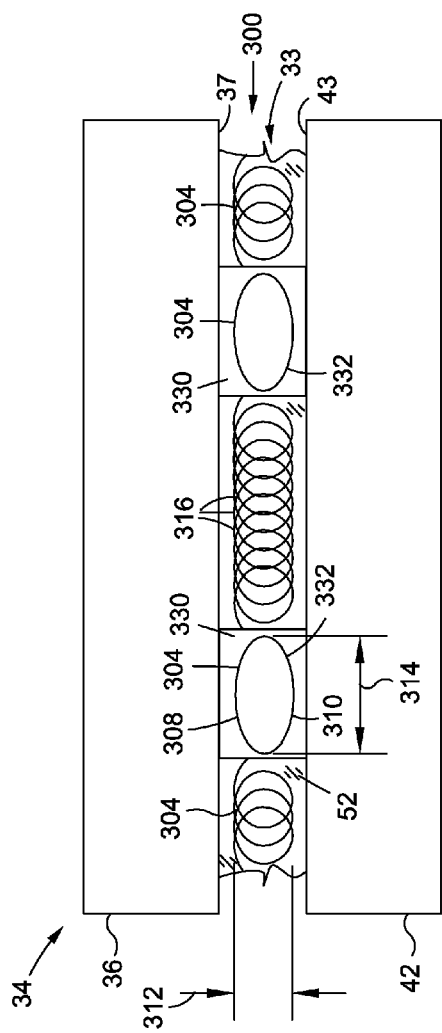
FIG. 15 is an illustration of a partial cross-sectional view of another embodiment of the current sensor network wherein the inductive coils have an oval cross-sectional shape.

FIG. 15 shows a partial cross-sectional view of another embodiment of the current sensor network 302 wherein the inductive coils 304 have an oval cross-sectional shape 322 when viewed from an end of the inductive coil 304 along a lengthwise direction of the inductive coil 304. As may be appreciated, the inductive coils 304 may be provided in any one of a variety of different cross-sectional sizes, shapes and configurations, and are not limited to the rectangular and oval cross-sectional shapes 320, 322 shown in FIGS. 14 and 15. For example, one or more of the inductive coils 304 may have a square cross-sectional shape, a triangular cross-sectional shape, and/or other cross-sectional shapes or combinations thereof.

A current detection system 300 may be incorporated into a structural assembly 34 using a manufacturing method which may include providing a first structure 36 and a second structure 42 to be adhesively bonded together. The method may include preparing the first faying surface 37 of the first structure 36 for bonding such as by abrading the first faying surface 37 to improve the adhesive capability, and may include cleaning and/or treating the first faying surface 37 to facilitate the adhesive bonding process. The second faying surface 43 of the second structure 42 may be prepared for bonding in a similar manner to the first faying surface 37 of the first structure 36. The method may additionally include installing a current sensor network 302 as described above on the first faying surface 37 of the first structure 36. The method may additionally include connecting the current sensor nodes 330 to the digital data communications network 76 using signal wire 342 as shown in FIG. 12. The signal wires 342 may electrically connect one or more of the current sensor nodes 330 to one or more of the current integrators 346. The method may additionally include covering a substantial majority of the first faying surface 37 area with an adhesive layer 52. In this regard, the method may include applying an adhesive layer 52 to the first faying surface 37 in a manner to embed the inductive coils 304 and the current sensor nodes 330 in the adhesive layer 52. The method may further include positioning the second structure 42 over the first structure 36 such that the second faying surface 43 is in contact with the adhesive layer 52. The method may also include allowing the adhesive layer 52 to cure such that the first structure 36 is adhesively bonded to the second structure 42 with the current sensor network 302 embedded within the adhesive layer 52.

Figure 16:
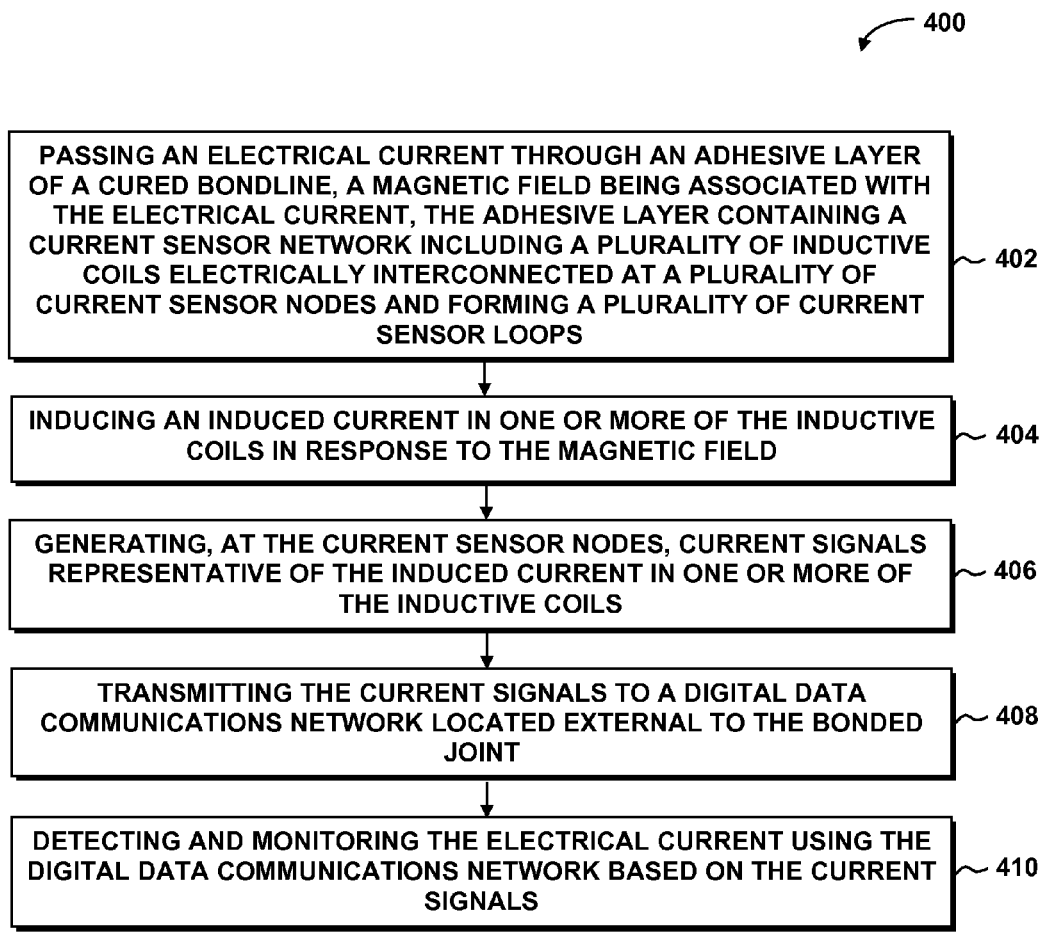
FIG. 16 is an illustration of a flow diagram of an embodiment of a method for monitoring electrical current flow through a cured on line of the bonded structural assembly.

FIG. 16 is an illustration of a flow diagram of an embodiment of a method 400 for detecting and monitoring electrical current 350 flow through a cured bondline 32 of a structural assembly 34. Step 402 of the method 400 may include passing an electrical current 350 through an adhesive layer 52 of a cured bondline 32 of the structural assembly 34. As indicated above, the electrical current 350 may have a magnetic field 352 associated therewith. The electrical current 350 may be a relatively high-intensity transient electrical current or pulse passing through the cured bondline 32. In some examples, the high-intensity transient electrical current or pulse may be the result of a lightning strike on an aircraft containing the structural assembly 34. The structural assembly 34 may include a cured bondline 32 containing an adhesive layer 52 within which a current sensor network 302 may be embedded. As indicated above, the current sensor network 302 may include a plurality of inductive coils 304 electrically interconnected at a plurality of current sensor nodes 330 and forming a plurality of current sensor loops 338.

Step 404 of the method 400 may include inducing an induced current 306 in the current sensor loops 338 in response to the magnetic field 352 associated with the electrical current 350 passing through the cured bondline 32. As indicated above, the magnetic field 352 may induce a relatively low-amperage induced current 306 in one or more of the inductive coils 304 of the current sensor network 302. As mentioned above, the inductive coils 304 may have a relatively low profile or height so that the inductive coils 304 may fit within a relatively thin bondline associated with adhesively-bonded joints 33. In this regard, the inductive coils 304 may be provided with a generally flattened cross-sectional shape 318 in order to increase the area of the inductive profile, and thereby may enhance the ability of the inductive coils 304 to pick up the magnetic field 352 such that an induced current 306 may be generated in the inductive coils 304.

Step 406 of the method 400 may include generating, at the current sensor nodes 330, current signals 344 representative of the induced current 306. In some examples, one or more of the current sensor nodes 330 may include electronic circuitry or logic for converting the induced current 306 into current signals 344. A current signal 344 generated by a current sensor node 330 may be proportional to or representative of the induced current 306 in the inductive coils 304. For example, a current signal 344 may represent the amperage of the induced current 306 in the inductive coil 304 that terminates at the current sensor node 330.

Step 408 of the method 400 may include transmitting one or more of the current signals 344 to a digital data communications network 76 which may be located external to the cured bondline 32. In this regard, the current sensor nodes 330 may be electrically connected to one or more current integrators 346 associated with a data retrieval system 78 of the digital data communications network 76. In some examples, each one of the current sensor nodes 330 may be electrically connected via a signal wire 342 to a dedicated current integrator 346 which may be located external to the cured bondline 32. However, in some examples, the current integrators 346 may be incorporated into the current sensor nodes 330, and the signal wires 342 may transmit current signals 344 from the current sensor nodes 330 to a data processing system 80 of the digital data communications network 76.

Step 410 of the method 400 may include detecting and monitoring the electrical current 350 using the digital data communications network 76 based on the current signals 344. As indicated above, the digital data communications network 76 may be configured to detect the presence of an electrical current 350 passing through the cured bondline 32. For example, the digital data communications network 76 may compare the summed total of the magnitude of the individual current signals 344 to a predetermined baseline or threshold current value. When the summed total of the individual currents exceeds the threshold current value, the digital data communications network 76 may indicate in real time or recorded time that an electrical current 350 is passing through or has passed through one or more portions of the cured bondline 32. In some examples, a current profile of the electrical current 350 may be displayed or plotted on an oscilloscope (e.g., plotting plot the amperage over time) as may be included with the digital data communications network 76.

In some examples, the method may include determining a relative magnitude of the electrical current 350 passing through the adhesive layer 52 at locations adjacent to the current sensor nodes 330 based upon the relative magnitude of the current signals transmitted from each current sensor node 330. In another example, the method may include summing the output signals 348 generated by each one of the current integrators 346, and determining the total electrical charge passing through the cured bondline 32 during an electrical current 350 event (e.g., during an actual or simulated lightning strike) based on the output signals 348. In this manner, the current sensor network 302 may provide a means for determining the severity of a lightning strike in terms of absolute magnitude and/or relative magnitude of the total electric charge associate with the electrical current 350. Based upon the magnitude of the total electric charge measured at the bonded joint 33, a determination may be made regarding whether inspection of the bonded joint 33 is necessary.

In some examples, the method may include determining the electrical current 350 passing through one or more bonded joints 33 of a vehicle such as an aircraft 10. In this regard, the method may include providing certain bonded joints 33 with a current sensor network 302 in the cured bondline 32. Each one of the current sensor networks 302 may be electrically connected to a digital data communications network 76 and/or to an IVHM system 124. The bonded joints 33 may be monitored with a time stamp to enable the determination of flow direction and/or direction of propagation of an electrical charge as it passes through a structure such as through an aircraft subjected to a lighting strike or other high-intensity electrical charge. Determining the flow path of electrical charge through a structure such as an aircraft may assist in identifying a location of the lightning strike on the aircraft and identifying the bonded joints 33 that were subjected to high-intensity electrical current 350 associated with the lightning strike. A similar current detection system 300 and method may be incorporated into any type of structure, without limitation, including any type of vehicular or non-vehicular structure.

Many modifications and other embodiments of the disclosure will come to mind to one skilled in the art to which this disclosure pertains having the benefit of the teachings presented in the foregoing descriptions and the associated drawings. The embodiments described herein are meant to be illustrative and are not intended to be limiting or exhaustive. Although specific terms are employed herein, they are used in a generic and descriptive sense only and not for purposes of limitation.

What is claimed is:

1. A system for monitoring electrical current passing through a cured bondline of a bonded joint, the system comprising:
 a current sensor network embedded in an adhesive layer of a cured bondline of a structural assembly, including:
  a plurality of inductive coils; and
  a plurality of current sensor nodes electrically interconnecting the inductive coils to form a plurality of current sensor loops generating induced current in response to a magnetic field associated with an electrical current passing through the adhesive layer, the current sensor nodes generating current signals representative of the induced current;

a digital data communications network located external to the cured bondline and receiving the current signals from the current sensor nodes and detecting and monitoring electrical current passing through the cured bondline based on the current signals.

2. The system of claim 1, wherein:
the adhesive layer comprises an epoxy adhesive, a polyurethane adhesive, and/or an acrylic adhesive.

3. The system of claim 1, wherein:
the structural assembly comprises a first structure formed of composite material, metallic material, or a combination thereof, bonded at the cured bondline to a second structure made of composite material, metallic material, or a combination thereof.

4. The system of claim 1, wherein:
the current sensor nodes are arranged such that the current sensor loops form a grid pattern in the cured bondline.

5. The system of claim 1, wherein:
at least some of the inductive coils are oriented generally orthogonally relative to one another such that at least one of the current sensor loops has a square shape defined by an inductive coil on each of four sides of the current sensor loop and having a current sensor node at each corner.

6. The system of claim 1, wherein:
the digital data communications network includes a data retrieval system and a data processing system;
the data retrieval system including one or more current integrators electrically connected to the current sensor nodes and integrating the induced current over time and generating one or more output signals; and
the data processing system determining a total electrical charge passing through the cured bondline based on the output signals.

7. The system of claim 1, wherein:
the inductive coils have an inductive coil height of no greater than approximately 0.020 inch, the inductive coil height being less than a bondline thickness of the cured bondline.

8. The system of claim 1, wherein:
the inductive coils have a flattened cross-sectional shape and an inductive coil height that is less than an inductive coil width.

9. The system of claim 8, wherein:
the flattened cross-sectional shape is a rectangular cross-sectional shape or an oval cross-sectional shape when the inductive coil is viewed from an end along a lengthwise direction of the inductive coil.

10. An aircraft, comprising:
a structural assembly including at least one bonded joint having an adhesive layer in a cured bondline bonding a first structure to a second structure;
a current sensor network embedded in an adhesive layer of the cured bondline, including:
a plurality of inductive coils generating induced current in response to a magnetic field associated with an electrical current passing through the adhesive layer; and
a plurality of current sensor nodes electrically interconnecting the inductive coils to form a plurality of current sensor loops, the current sensor nodes generating current signals representative of the induced current; and a digital data communications network located external to the cured bondline and receiving the current signals from the current sensor network and detecting and monitoring electrical current passing through the cured bondline based on the current signals.

11. A method for monitoring electrical current passing through a cured bondline, comprising:
passing an electrical current through an adhesive layer of a cured bondline of a structural assembly, the electrical current having a magnetic field associated therewith, the adhesive layer containing a current sensor network including a plurality of inductive coils electrically interconnected at a plurality of current sensor nodes and forming a plurality of current sensor loops;
inducing an induced current in the current sensor loops in response to the magnetic field;
generating, at the current sensor nodes, current signals representative of the induced current;
transmitting the current signals to a digital data communications network located external to the cured bondline;
detecting and monitoring the electrical current using the digital data communications network based on the current signals.

12. The method of claim 11, wherein the step of detecting and monitoring the electrical current includes:
determining a relative magnitude of the electrical current passing through the adhesive layer based upon the current signals at the current sensor nodes; and
determining a distribution of the electrical current passing through the adhesive layer based upon the relative magnitude of the current signals.

13. The method of claim 11, wherein:
the electrical current is a result of a lightning strike on an aircraft containing the structural assembly.

14. The method of claim 11, wherein the steps of transmitting the current signals and detecting and monitoring the electrical current include:
transmitting the current signals from the current sensor nodes to one or more current integrators;
integrating, using the current integrators, the induced current over time to form output signals representative of the current signals; and
determining a total electrical charge passing through the cured bondline based on the output signals.

15. The method of claim 11, wherein the step of monitoring the electrical current include:
determining an electrical current profile of the electrical current passing through the adhesive layer.

16. The method of claim 11, wherein:
the adhesive layer comprises an epoxy adhesive, a polyurethane adhesive, and/or an acrylic adhesive.

17. The method of claim 11, wherein:
the structural assembly comprises a first structure formed of composite material, metallic material, or a combination thereof, bonded at the cured bondline to a second structure made of composite material, metallic material, or a combination thereof.

18. The method of claim 11, wherein:
the current sensor nodes are arranged such that the current sensor loops form a grid pattern in the cured bondline.

19. The method of claim 11, wherein:
the inductive coils have an inductive coil height of no greater than approximately 0.020 inch, the inductive coil height being less than a bondline thickness of the cured bondline.

20. The method of claim 11, wherein:
the inductive coils have a flattened cross-sectional shape such that an inductive coil height is less than an inductive coil width.

* * * * *